US012583938B2

(12) United States Patent (10) Patent No.: US 12,583,938 B2
Schneider et al. (45) Date of Patent: Mar. 24, 2026

(54) PROTEIN BIOMARKER AND USES THEREOF

(71) Applicants: Daiichi Sankyo Co., Ltd., Tokyo (JP); Daiichi Sankyo Europe GmbH, Munich (DE); Kinki University, Osaka (JP); Amgen, Inc., Thousand Oaks, CA (US)

(72) Inventors: Matthias Schneider, Neufarn (DE); Sabine Blum, Munich (DE); Renee Jeanne Mendell-Harary, Skillman, NJ (US); Daniel J. Freeman, Holmdel, NJ (US); Robert Allen Beckman, Blue Bell, PA (US); Xiaoping Jin, Hillsborough, NJ (US); Kimio Yonesaka, Osakasayama (JP); Kazuhiko Nakagawa, Osakasayama (JP)

(73) Assignees: Daiichi Sankyo Co., Ltd., Tokyo (JP); Daiichi Sankyo Europe GmbH, Munich (DE); Kinki University, Osaka (JP); Amgen, Inc., Thousand Oaks, CA (US)

( * ) Notice: Subject to any disclaimer, the term of this patent is extended or adjusted under 35 U.S.C. 154(b) by 217 days.

(21) Appl. No.: 18/388,099

(22) Filed: Nov. 8, 2023

(65) Prior Publication Data

US 2024/0084037 A1 Mar. 14, 2024

Related U.S. Application Data

(60) Division of application No. 16/547,440, filed on Aug. 21, 2019, now Pat. No. 11,873,344, which is a continuation of application No. 15/297,793, filed on Oct. 19, 2016, now abandoned, which is a continuation of application No. 14/502,769, filed on Sep. 30, 2014, now abandoned.

(60) Provisional application No. 61/884,983, filed on Sep. 30, 2013.

(51) Int. Cl.

| | |
|---|---|
| G01N 33/574 | (2006.01) |
| A61K 31/517 | (2006.01) |
| A61K 39/395 | (2006.01) |
| A61K 45/06 | (2006.01) |
| A61N 5/10 | (2006.01) |
| C07K 16/28 | (2006.01) |
| C07K 16/32 | (2006.01) |
| C07K 16/40 | (2006.01) |
| G01N 33/569 | (2006.01) |
| A61K 39/00 | (2006.01) |

(52) U.S. Cl.
CPC ............ *C07K 16/32* (2013.01); *A61K 31/517* (2013.01); *A61K 39/39558* (2013.01); *A61K 45/06* (2013.01); *A61N 5/10* (2013.01); *C07K*
*16/2863* (2013.01); *C07K 16/40* (2013.01); *G01N 33/5695* (2013.01); *G01N 33/57423* (2013.01); *A61K 2039/505* (2013.01); *C07K 2317/21* (2013.01); *C07K 2317/76* (2013.01); *G01N 2333/4756* (2013.01)

(58) Field of Classification Search
CPC ................. G01N 33/57423; G01N 2333/4756
See application file for complete search history.

(56) References Cited

U.S. PATENT DOCUMENTS

| | | | |
|---|---|---|---|
| 6,140,110 | A | 10/2000 | Vinayagamoorthy et al. |
| 9,766,249 | B2 | 9/2017 | Clark et al. |
| 2001/0046686 | A1 | 11/2001 | Wong et al. |
| 2006/0019407 | A1 | 1/2006 | Fulton et al. |
| 2008/0172184 | A1 | 7/2008 | Chaires et al. |
| 2011/0027291 | A1 | 2/2011 | Schoeberl et al. |

(Continued)

FOREIGN PATENT DOCUMENTS

| | | |
|---|---|---|
| WO | WO 2013/023043 A2 | 2/2013 |
| WO | WO 2013/052745 A2 | 4/2013 |

OTHER PUBLICATIONS

"Biomarkers and surrogate endpoints: preferred definitions and conceptual framework", Biomarkers Definitions Working Group, Clinical Pharmacol. Ther. (Mar. 2001), vol. 69, vol. 3, pp. 89-95.

(Continued)

*Primary Examiner* — Mark Halvorson
(74) *Attorney, Agent, or Firm* — FOLEY & LARDNER LLP

(57) ABSTRACT

The present invention is directed to methods of identifying and treating a human subject harboring a tumor or other disease comprising assessing HRG gene expression at a protein level in the human subject and administering a treatment comprising an anti-HER3 antibody to the human subject whose HRG gene expression at a protein level is assessed as high. The present invention is also directed to methods of identifying a human subject harboring a tumor or other disease comprising assessing HRG gene expression at a protein level in the human subject and withholding a treatment comprising an anti-HER3 antibody to the human subject whose HRG gene expression at a protein level is assessed as low. The invention is also directed to methods of performing an ELISA, including sequential steps of contacting a solid surface with a plurality of solutions each comprising in turn a capture antibody, a blocking agent, a sample suspected of containing an analyte, a detection antibody and an enzyme conjugate, in which the solid surface is subjected to a wash process after each sequential step.

8 Claims, 10 Drawing Sheets

(56) References Cited

U.S. PATENT DOCUMENTS

| | | | |
|---|---|---|---|
| 2011/0039308 A1 | 2/2011 | Slupska et al. | |
| 2011/0059076 A1 | 3/2011 | Mcdonagh et al. | |
| 2012/0164627 A1 | 6/2012 | Battrell et al. | |
| 2013/0203725 A1 | 8/2013 | Breitz et al. | |
| 2015/0231238 A1* | 8/2015 | Garcia | A61P 35/00 |
| | | | 424/133.1 |

OTHER PUBLICATIONS

Cho, "Contribution of oncoproteomics to cancer biomarker discovery" Molecular Cancer (2007), vol. 6, No. 25, pp. 1-13.

Engelman, et al. "The role of the ErbB family members in non-small cell lung cancers sensitive to epidermal growth factor receptor kinase inhibitors." Clin. Cancer Res. (2006) vol. 12, pp. 4372-4376.

International Search Report and Written Opinion of the International Searching Authority issued in International Application No. PCT/US14/58460 dated Mar. 13, 2015.

Ritter, et al. "Human breast cancer cells selected for resistance to trastuzumab In vivo overexpress epidermal growth factor receptor and ErbB ligands and remain dependent on the ErbB receptor network" Clin. Cancer Res. (2007), vol. 13, pp. 4909-4919.

Sawyers, "Overview Article the cancer biomarker problem" Nature (Apr. 3, 2008) vol. 452, pp. 548-552.

Sergina, et al. "Escape from HER-family tyrosine kinase inhibitor therapy by the kinase-inactive HER3" Nature (2007) vol. 445, pp. 437-441.

Paul, Fundamental Immunology, $3^{rd}$ Edition, 1993, pp. 292-295.

Rudikoff et al., Proc. Natl. Acad. Sci., vol. 79, No. 6, pp. 1979-1983 (1982).

Coleman, Research Immunology, vol. 145, pp. 33-36 (1994).

Yonesaka et al., Cancer Research, (Apr. 15, 2012) vol. 72, No. 8, Supp. 1, Abstract No. 4833.

Yonesaka, et al., "Heregulin as a novel cetuximab-resistance factor in colorectal cancer," J. Clin. Oncol., vol. 28 (15 Suppl), e14044 (2010), 4 pages.

LoRusso et al., "Phase I Study of U3-1287, a Fully Human Anti-HER3 Monoclonal Antibody, in Patients with Advanced Solid Tumors," Clin Cancer Research, vol. 19, pp. 3078-3087 (2013).

* cited by examiner

PROTEIN BIOMARKER AND USES THEREOF

CROSS-REFERENCE TO RELATED APPLICATIONS

This application is a divisional of U.S. patent application Ser. No. 16/547,440, filed Aug. 21, 2019, which is the continuation of U.S. patent application Ser. No. 15/297,793, filed Oct. 19, 2016, abandoned, which is a continuation of U.S. patent application Ser. No. 14/502,769, filed Sep. 30, 2014, abandoned, which claims priority from U.S. Provisional Patent Application No. 61/884,983, filed Sep. 30, 2013. The contents of these applications are incorporated herein by reference in their entirety.

FIELD OF THE INVENTION

The field of the invention is molecular biology, oncology, clinical diagnostics, clinical treatment, and methods of performing an enzyme-linked immunosorbent assay (ELISA) are also described herein.

BACKGROUND

Most cancer drugs are effective in some patients, but not in others. This results from genetic variation among tumors, and can be observed even among tumors within the same patient. Variable patient response is particularly pronounced with respect to targeted therapeutics. Therefore, the full potential of targeted therapies cannot be realized without suitable tests for determining which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention." (Biomarkers Definitions Working Group, 2001, Clin. Pharmacol. Ther. 69:89-95)

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states: "There is a critical need for expedited development of biomarkers and their use to improve diagnosis and treatment of cancer." (Cho, 2007, Molecular Cancer 6:25) Another recent review article on cancer biomarkers contains the following comments: "The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, Nature 452:548-552, at 548) Comments such as the foregoing illustrate the recognition of a need for the discovery of clinically useful biomarkers and diagnostic methods based on such biomarkers.

There are three distinct types of cancer biomarkers: (1) prognostic biomarkers, predictive biomarkers, and (3) pharmacodynamic biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2) gene is amplified are likely to benefit from treatment with trastuzumab (HERCEPTIN®), whereas patients without ERBB2 gene amplification are unlikely to benefit from treatment with trastuzumab. A pharmacodynamic biomarker is an indication of the effect(s) of a drug on its molecular target while the patient is taking the drug. Accordingly, pharmacodynamic biomarkers often are used to guide dosage level and dosing frequency, during the early stages of clinical development of a new drug. For a discussion of cancer biomarkers, see, e.g., Sawyers, 2008, Nature 452:548-552.

Tumors driven by EGFR or HER2 often respond to treatment with inhibitors of EGFR or HER2, but these tumors invariably develop resistance to these inhibitors. At least one mechanism of acquired resistance to anti-EGFR or anti-HER2 treatment is activation of HER3 (also known as ERBB3) signaling. See, e.g., Engelman et al, 2006, Clin. Cancer Res. 12:4372; Ritter et al, 2007, Clin. Cancer Res. 13:4909; Sergina et al, 2007, Nature 445:437. HER3 plays an important role in development of drug resistance, as well as being involved in tumor initiation and maintenance, through its heterodimerization with EGFR and HER2. Consequently, there has been interest in development of HER3 inhibitors, especially anti-HER3 antibodies, since HER3 lacks kinase activity.

As with other types of targeted therapy, some, but not all, tumors respond to anti-HER3 therapy. Therefore, there is a need for diagnostic methods based on predictive biomarkers that can be used to identify patients with tumors that are likely (or unlikely) to respond to treatment with a HER3 inhibitor such as an anti-HER3 antibody.

SUMMARY

The present invention is directed to methods of treating a human subject harboring a locally advanced or metastatic non-small cell lung cancer (NSCLC) tumor comprising administering a treatment comprising an anti-HER3 antibody to a human subject diagnosed with a locally advanced or metastatic NSCLC whose HRG gene expression at a protein level is assessed as high.

Some embodiments comprise assessing HRG gene expression at a protein level in a human subject diagnosed with a locally advanced or metastatic NSCLC and administering a treatment comprising an anti-HER3 antibody to a human subject whose HRG gene expression at a protein level is assessed as high.

Some embodiments comprise ordering an assessment of HRG gene expression at a protein level in a human subject diagnosed with a locally advanced or metastatic NSCLC and administering a treatment comprising an anti-HER3 anti-body to the human subject whose HRG gene expression at a protein level is assessed as high.

In a particular embodiment of the invention, the HRG gene expression a protein level is assessed as high if a protein concentration value is observed, which is above a predetermined threshold, from a biological sample taken from the subject diagnosed with a locally advanced or metastatic NSCLC.

In some embodiments, the predetermined threshold is chosen statistically to minimize undesirable effects of false positives and false negatives. In a preferred embodiment, the predetermined threshold value is selected from the group consisting of about 0 pg/mL, about 980 pg/mL, about 1622 pg/mL, about 2000 pg/mL, about 3000 pg/mL, about 4000 pg/mL, and about 5000 pg/mL.

In some embodiments, the subject harbors wild-type EGFR. In preferred embodiments, the tumor has also pro-gressed on at least one prior systemic therapy. In more preferred embodiments, a tumor tissue or fragment thereof for or with which the HRG gene expression is assessed had been removed from the subject prior to any (systemic) therapy.

Some embodiments comprise assessing HRG gene expression at a protein level in a human subject diagnosed with a locally advanced or metastatic NSCLC, where HRG gene expression at a protein level is assessed using ELISA or immunohistochemistry techniques.

In some embodiments, the biological sample comprises a whole blood or serum sample.

In some embodiments, the anti-HER3 antibody is selected from the group consisting of patritumab, duligotumab (MEI-ID-7945A), seribantumab (MM-121), MM-111, LJM716, RG-7116, tri-specific anti-EGRF/ERBB3 zybody, huHER3-8, or a derivative or fragment of any of these.

In some embodiments, the treatment comprises an anti-HER3 antibody in combination with one or more of (i) a HER inhibitor, (ii) a chemotherapy, (iii) radiation, and (iv) an other targeted agent.

For example, in some embodiments the HER inhibitor is selected from the group consisting of trastuzumab, T-DM1, lapatinib, pertuzumab, cetuximab, panitumumab gefitinib, afatinib, dacomitinib, KD-019 and erlotinib.

In some embodiments, the chemotherapy is selected from the group consisting of cisplatin, carboplatin, gemcitabine, pemetrexed, irinotecan, 5-fluoruracil, paclitaxel, docetaxel, and capecitabine. However, other chemotherapies can be applied.

The present invention is also directed to methods of treating a human subject harboring a locally advanced or metastatic non-small cell lung cancer (NSCLC) tumor com-prising assessing HRG gene expression at a protein level in a human subject diagnosed with a locally advanced or metastatic NSCLC, and withholding a treatment comprising an anti-HER3 antibody to a human subject whose HRG gene expression at a protein level is assessed as low.

Some embodiments comprise ordering an assessment of an HRG gene expression at a protein level in a human subject diagnosed with a locally advanced or metastatic NSCLC and withholding a treatment comprising an anti-HER3 antibody to the human subject whose HRG gene expression at a protein level is assessed as low.

In some embodiments, the HRG gene expression at a protein level is assessed as low if a protein concentration value is observed, which is at or below a predetermined threshold, from a biological sample taken from the subject diagnosed with a locally advanced or metastatic NSCLC.

In some embodiments, the predetermined threshold is chosen statistically to minimize undesirable effects of false positives and false negatives. In some embodiments, the predetermined threshold value is selected from the group consisting of 0 pg/mL, about 980 pg/mL, about 1000 pg/mL, about 1622 pg/mL, about 2000 pg/mL, about 3000 pg/mL, about 4000 pg/mL, and about 5000 pg/mL.

In some, embodiments, the subject harbors wild-type EGFR. In preferred embodiments, the tumor has progressed on at least one prior systemic therapy. In more preferred embodiments, a tumor tissue or fragment thereof for or with which the HRG gene expression is assessed has been removed from the subject prior to any (systemic) therapy.

In some embodiments, HRG gene expression at a protein level is assessed using ELISA or immunohistochemistry techniques.

In some embodiments, the biological sample comprises a whole blood or serum sample.

In some embodiments, the treatment withheld comprises an anti-HER3 antibody in combination with one or more of (i) a HER inhibitor, (ii) a chemotherapy, (iii) radiation, and (iv) an other targeted agent.

Some embodiments comprise treating a human subject whose HRG gene expression at a protein level is assessed as low with a HER inhibitor selected from the group consisting of trastuzumab, T-DM1, lapatinib, pertuzumab, cetuximab, panitumumab gefitinib, afatinib, dacomitinib, KD-019 and erlotinib.

Some embodiments comprise treating a human subject whose HRG gene expression at a protein level is assessed as low with a chemotherapy selected from the group consisting of cisplatin, carboplatin, gemcitabine, pemetrexed, irinote-can, 5-fluoruracil, paclitaxel, docetaxel, and capecitabine. However, other chemotherapies can be applied.

Some embodiments comprise treating a human subject whose HRG gene expression at an mRNA level is assessed as low or high with crizotinib. In some embodiments, the subject treated with crizotinib has an ALK gene rearrange-ment or fusion.

The invention is also directed to kits for facilitating an assessment of HRG gene expression at a protein level.

The invention is also directed to methods of identifying a human patient diagnosed with a locally advanced or meta-static non-small cell lung cancer (NSCLC) who is likely to benefit from a treatment comprising an anti-HER3 antibody comprising obtaining a biological sample from a human patient diagnosed with a locally advanced or metastatic NSCLC, using the sample, determining a value for HRG gene expression at a protein level in the human patient, and, optionally, recording the value determined.

Some embodiments comprise receiving a biological sample from a human patient diagnosed with a locally advanced or metastatic NSCLC; using the sample, deter-mining a value for HRG gene expression at a protein level in the human subject; and, optionally, recording the value determined.

Some embodiments comprise assessing if the value deter-mined is below, at, or above a predetermined threshold value. In some embodiments, the predetermined threshold value is selected from the group consisting of 0 pg/mL, about 980 pg/mL, about 1000 pg/mL, about 1622 pg/mL, about 2000 pg/mL, about 3000 pg/mL, about 4000 pg/mL, and about 5000 pg/mL.

Some embodiments involve characterizing the HRG gene expression at a protein level as high if the value determined is above the predetermined threshold value.

Some embodiments involve characterizing the HRG gene expression at a protein level as low if the value determined is at or below the predetermined threshold value.

Some embodiments comprise reporting the value determined to an attending physician or other medical practitioner.

In some embodiments, the sample comprises a whole blood or serum sample.

In some embodiments, the subject does not harbor an epidermal growth factor receptor (EGFR) sensitizing mutation. In preferred embodiments, the subject harbors wild-type EGFR. In even more preferred embodiments, the tumor has progressed on at least one prior systemic therapy. In more preferred embodiments, a tumor tissue or fragment thereof for or with which the HRG gene expression is assessed has been removed from the subject prior to any (systemic) therapy.

In some embodiments, the treatment comprises an anti-HER3 antibody in combination with one or more of (i) a HER inhibitor, (ii) a chemotherapy, (iii) radiation, and (iv) an other targeted agent.

The invention is also directed to methods where HRG gene expression is assessed as high based on randomized clinical data.

The invention is also directed to methods of receiving or undergoing a treatment for a locally advanced or metastatic non-small cell lung cancer (NSCLC) tumor or abstaining therefrom. In some embodiments, the methods comprise providing an autologous tissue sample or consenting to a taking of same to facilitate an assessment of HRG gene expression at a protein level in a human subject diagnosed with a locally advanced or metastatic NSCLC; and receiving a treatment comprising an anti-HER3 antibody if HRG gene expression at a protein level is assessed as high, or abstaining from a treatment comprising an anti-HER3 antibody if HRG gene expression at a protein level is assessed as low.

The invention is also directed to methods of electing a treatment for a locally advanced or metastatic non-small cell lung cancer (NSCLC) tumor. In some embodiments, the methods comprise receiving an assessment of HRG gene expression at a protein level in a human subject diagnosed with a locally advanced or metastatic NSCLC; and electing to withhold a treatment comprising an anti-HER3 antibody if HRG gene expression at a protein level is assessed as low, or electing to administer a treatment comprising an anti-HER3 antibody if HRG gene expression at a protein level is assessed as high.

The invention is also directed to methods of performing an ELISA, including sequential steps of contacting a solid surface with a plurality of solutions each comprising in turn a capture antibody, a blocking agent, a sample suspected of containing an analyte, a detection antibody and an enzyme conjugate, in which the solid surface is subjected to a wash process after each sequential step, the wash process comprising (a) cycling wash buffer on and off the solid surface at a rapid rate until bubbles are observed at which point the cycled wash buffer is removed, (b) optionally repeating step (a) using fresh wash buffer; and (c) rinsing the solid surface with fresh wash buffer, provided that after completing the wash process following the enzyme conjugate sequential step, the solid surface is contacted with a solution comprising an enzyme substrate.

Some embodiments comprise adding to the solid surface a stop solution.

Some embodiments comprise obtaining a spectrophotometric reading to obtain a measure of an amount of analyte present in the sample, if any.

In some embodiments, the wash buffer comprises a surfactant.

In some embodiments, the wash buffer comprises phosphate buffered saline (PBS).

In preferred embodiments, the wash buffer has a pH ranging from 7.2-7.4.

In some embodiments, the cycling step comprises applying and aspirating the wash buffer on and off the solid surface using a "piston" action.

In some embodiments, the wash buffer is cycled 20 or more times on and off the solid surface.

In some embodiments, the rinsing step of the wash process removes substantially all bubbles on the solid surface.

In some embodiments, the solution comprising the detection antibody excludes normal goat serum.

In some embodiments, the "piston" action is facilitated by use of a pipette.

In some embodiments, the capture antibody and the detection antibody specifically recognize human heregulin (HRG).

In some embodiments, the solution comprising the sample comprises undiluted serum or undiluted plasma.

In some embodiments, the capture antibody is mouse anti-human HRG.

In some embodiments, the detection antibody is biotinylated goat anti-human HRG.

In some embodiments, the enzyme conjugate is streptavidin-horse radish peroxidase.

In some embodiments, the enzyme substrate is a mixture of hydrogen peroxide and tetramethylbenzidine.

In some embodiments, the solid surface is contacted with the solution comprising the capture antibody for at least 8 hours at a temperate in the range of about 65° to 80° F.

In some embodiments, the solution comprising the blocking agent comprises 1% bovine serum albumin in phosphate buffered saline at a pH in the range of 7.2 to 7.4.

In some embodiments, the solid surface is contacted with the solution comprising the blocking agent for at least one hour at a temperate in the range of about 65° to 80° F.

In some embodiments, the solid surface is contacted with the solution comprising the sample for about 2 hours at a temperate in the range of about 65° to 80° F.

In some embodiments, the solid surface is contacted with the solution comprising the detection antibody for about 2 hours at a temperate in the range of about 65° to 80° F.

In some embodiments, the solid surface is contacted with the solution comprising the enzyme conjugate for about 20 minutes at a temperate in the range of about 65° to 80° F.

In some embodiments, the solid surface is contacted with the solution comprising the enzyme substrate for about 20 minutes at a temperate in the range of about 65" to 80° F., In some embodiments, the solid surface is a microplate comprising one or more wells.

In some embodiments, the cycling step (a) is performed two times before performing the rinsing step (c).

In some embodiments, the surfactant is polyethylene glycol sorbitan monolaurate.

The present invention includes the following (1) to (114), but is not limited thereto.

(1) A method of treating a human subject harboring a locally advanced or metastatic non-small cell lung cancer (NSCLC) tumor comprising:
    assessing HRG gene expression at a protein level in a human subject diagnosed with a locally advanced or metastatic NSCLC; and administering a treatment comprising an anti-HER3 antibody to a human subject whose HRG gene expression at a protein level is assessed as high.

(2) The method of (1) in which the HRG gene expression at a protein level is assessed as high if a protein concentration value is observed, which is above a predetermined threshold, from a biological sample taken from the subject diagnosed with a locally advanced or metastatic NSCLC.

(3) The method of (2) in which the predetermined threshold is chosen statistically to minimize undesirable effects of false positives and false negatives.

(4) The method of (1) in which the predetermined threshold value is selected from the group consisting of about 0 pg/mL, about 980 pg/mL, about 1622 pg/mL, about 2000 pg/mL, about 3000 pg/mL, about 4000 pg/mL, and about 5000 pg/mL.

(5) The method of (1), wherein the subject harbors wild-type EGFR.

(6) The method of (5), wherein the tumor has progressed on at least one prior systemic therapy.

(7) The method of (1) in which HRG gene expression at a protein level is assessed using ELISA or immunohistochemistry techniques.

(8) The method of (2) in which the biological sample comprises a whole blood or serum sample.

(9) The method of (1) in which the anti-HER3 antibody is selected from the group consisting of patritumab, duligotumab (MEHD-7945A), seribantumab (MM-121), MM-111, LJM716, RG-7116, tri-specific anti-EGFR/ERBB3 zybody, huHER3-8, or a derivative or fragment of any of these.

(10) The method of (1) in which the treatment comprises an anti-HER3 antibody in combination with one or more of (i) a HER inhibitor, (ii) a chemotherapy, (iii) radiation, and (iv) an other targeted agent.

(11) The method of (10), wherein the HER inhibitor is selected from the group consisting of trastuzumab, T-DM1, lapatinib, pertuzumab, cetuximab, panitumumab gefitinib, afatinib, dacomitinib, KD-019 and erlotinib.

(12) The method of (10), wherein the chemotherapy is selected from the group consisting of cisplatin, carboplatin, gemcitabine, pemetrexed, irinotecan, 5-fluorouracil, paclitaxel, docetaxel, and capecitabine.

(13) A method of treating a human subject harboring a locally advanced or metastatic non-small cell lung cancer (NSCLC) tumor comprising:

assessing HRG gene expression at a protein level in a human subject diagnosed with a locally advanced or metastatic NSCLC; and withholding a treatment comprising an anti-HER3 antibody to a human subject whose HRG gene expression at a protein level is assessed as low.

(14) The method of (13) in which the HRG gene expression at a protein level is assessed as low if a protein concentration value is observed, which is at or below a predetermined threshold, from a biological sample taken from the subject diagnosed with a locally advanced or metastatic NSCLC.

(15) The method of (14) in which the predetermined threshold is chosen statistically to minimize undesirable effects of false positives and false negatives.

(16) The method of (14) in which the predetermined threshold value is selected from the group consisting of 0 pg/mL, about 980 pg/mL, about 1622 pg/mL about 2000 pg/mL, about 3000 pg/mL about 4000 pg/mL, and about 5000 pg/mL.

(17) The method of (13), wherein the subject harbors wild-type EGFR.

(18) The method of (17), wherein the tumor has progressed on at least one prior systemic therapy.

(19) The method of (13) in which HRG gene expression at a protein level is assessed using ELISA or immunohistochemistry techniques.

(20) The method of (14) in which the biological sample comprises a whole blood or serum sample.

(21) The method of (13) in which the treatment withheld comprises an anti-HER3 antibody in combination with one or more of (i) a HER inhibitor, (ii) a chemotherapy, (iii) radiation, and (iv) an other targeted agent.

(22) The method of (13) further comprising treating a human subject whose HRG gene expression at a protein level is assessed as low with a HRG inhibitor selected from the group consisting of trastuzumab, T-DM1, lapatinib, pertuzumab, cetuximab, panitumumab gefitinib, afatinib, dacomitinib, KD-019 and erlotinib.

(23) The method of (13), further comprising treating a human subject whose HRG gene expression at a protein level is assessed as low with a chemotherapy selected from the group consisting of cisplatin, carboplatin, gemcitabine, pemetrexed, irinotecan, 5-fluoruracil, paclitaxel, docetaxel, and capecitabine.

(24) A kit for facilitating an assessment of HRG gene expression at a protein level.

(25) A method of identifying a human patient diagnosed with a locally advanced or metastatic non-small cell lung cancer (NSCLC) tumor who is likely to benefit from a treatment comprising an anti-HER3 antibody comprising:

obtaining a biological sample from a human patient diagnosed with a locally advanced or metastatic NSCLC;

using the sample, determining a value for HRG gene expression at a protein level in the human patient; and recording the value determined.

(26) The method of (25), further comprising assessing if the value determined is below at, or above a predetermined threshold value.

(27) The method of (26) in which the predetermined threshold value is selected from the group consisting of 0 pg/mL, about 980 pg/mL, about 1622 pg/mL, about 2000 pg/mL, about 3000 pg/mL, about 4000 pg/mL, and about 5000 pg/mL.

(28) The method of (26), further comprising characterizing the HRG gene expression at a protein level as high if the value determined is above the predetermined threshold value.

(29) The method of (26), further comprising characterizing the HRG gene expression at a protein level as low if the value determined is at or below the predetermined threshold value.

(30) The method of (25), further comprising reporting the value determined to an attending physician or other medical practitioner.

(31) The method of (25) in which the sample comprises a whole blood or serum sample.

(32) The method of (25), wherein the subject does not harbor an EGFR sensitizing mutation.

(33) The method of (25), wherein the subject harbors wild-type EGFR.

(34) The method of (33), wherein the tumor has progressed on at least one prior systemic therapy.

(35) The method of (25), wherein the treatment comprises an anti-HER3 antibody in combination with one or more of (i) a HER inhibitor, (ii) a chemotherapy, (iii) radiation, and (iv) an other targeted agent.

(36) A method of performing an ELISA, including sequential steps of contacting a solid surface with a plurality of solutions each comprising in turn a capture antibody, a blocking agent, a sample suspected of containing an analyte, a detection antibody and an enzyme conjugate, in which the solid surface is subjected to a wash process after each sequential step, the wash process comprising:

(a) cycling wash buffer on and off the solid surface at a rapid rate until bubbles are observed at which point the cycled wash buffer is removed;

(b) optionally repeating step (a) using fresh wash buffer; and (c) rinsing the solid surface with fresh wash buffer;

provided that after completing the wash process following the enzyme conjugate sequential step, the solid surface is contacted with a solution comprising an enzyme substrate.

(37) The method of (36) further comprising adding to the solid surface a stop solution.

(38) The method of (37) further comprising obtaining a spectrophotometric reading to obtain a measure of an amount of analyte present in the sample, if any.

(39) The method of (36) in which the wash buffer comprises a surfactant

(40) The method of (39) in which the wash buffer comprises phosphate buffered saline (PBS).

(41) The method of (40) in which the wash buffer has a pH ranging from 7.2-7.4.

(42) The method of (36) in which the cycling step comprises applying and aspirating the wash buffer on and off the solid surface using a "piston" action.

(43) The method of (42) in which the wash buffer is cycled 20 or more times on and off the solid surface.

(44) The method of (36) in which the rinsing step of the wash process removes substantially all bubbles on the solid surface.

(45) The method of (36) in which the solution comprising the detection antibody excludes normal goat serum.

(46) The method of (42) in which the "piston" action is facilitated by use of a pipette.

(47) The method of (36) in which the capture antibody and the detection antibody specifically recognize human heregulin (HRG).

(48) The method of (36) in which the solution comprising the sample comprises undiluted serum or undiluted plasma.

(49) The method of (47) in which the capture antibody is a mouse anti-human HRG antibody.

(50) The method of (49) in which the detection antibody is a biotinylated goat anti-human HRG antibody.

(51) The method of (50) in which the enzyme conjugate is streptavidin-horse radish peroxidase.

(52) The method of (51) in which the enzyme substrate is a mixture of hydrogen peroxide and tetramethylbenzidine.

(53) The method of (49) in which the solid surface is contacted with the solution comprising the capture antibody for at least 8 hours at a temperate in the range of about 65" to 80° F.

(54) The method of (36) in which the solution comprising the blocking agent comprises 1% bovine serum albumin in phosphate buffered saline at a pH in the range of 7.2 to 7.4.

(55) The method of (54) in which the solid surface is contacted with the solution comprising the blocking agent for at least one hour at a temperate in the range of about 65° to 80° F.

(56) The method of (48) in which the solid surface is contacted with the solution comprising the sample for about 2 hours at a temperate in the range of about 65° to 80° F.

(57) The method of (50) in which the solid surface is contacted with the solution comprising the detection antibody for about 2 hours at a temperate in the range of about 65° to 80° F.

(58) The method of (51) in which the solid surface is contacted with the solution comprising the enzyme conjugate for about 20 minutes at a temperate in the range of about 65° to 80° F.

(59) The method of (52) in which the solid surface is contacted with the solution comprising the enzyme substrate for about 20 minutes at a temperate in the range of about 65° to 80° F.

(60) The method of (36) in which the solid surface is a microplate comprising one or more wells.

(61) The method of (43) in which the cycling step (a) is performed two times before performing the rinsing step (c).

(62) The method of (40) in which the surfactant is polyethylene glycol sorbitan monolaurate.

(63) The method of any one of (1)-(35), wherein HRG gene expression is assessed as high based on randomized clinical data.

(64) A method of receiving or undergoing a treatment for a locally advanced or metastatic non-small cell lung cancer (NSCLC) tumor or abstaining therefrom comprising:

providing an autologous tissue sample or consenting to a taking of same to facilitate an assessment of HRG gene expression at a protein level in a human subject diagnosed with a locally advanced or metastatic NSCLC; and receiving or undergoing a treatment comprising an anti-HER3 antibody if HRG gene expression at a protein level is assessed as high, or abstaining from a treatment comprising an anti-HER3 antibody if HRG gene expression at a protein level is assessed as low.

(65) A method of electing a treatment for a locally advanced or metastatic non-small cell lung cancer (NSCLC) tumor comprising:

receiving an assessment of FIRE gene expression at a protein level in a human subject diagnosed with a locally advanced or metastatic NSCLC; and electing to withhold or abstain from a treatment comprising an anti-HER3 antibody if HRG gene expression at a protein level is assessed as low, or electing to receive or undergo a treatment comprising an anti-HER3 antibody if HRG gene expression at a protein level is assessed as high.

(66) A method of identifying a human patient diagnosed with a locally advanced or metastatic non-small cell lung cancer (NSCLC) who is likely to benefit from a treatment comprising an anti-HER3 antibody comprising:

receiving a biological sample from a human patient diagnosed with a locally advanced or metastatic NSCLC;

using the sample, determining a value for HRCT gene expression at a protein level in the human patient; and optionally, recording the value determined.

(67) A method of treating a human subject harboring a locally advanced or metastatic non-small cell lung cancer (NSCLC) tumor comprising:

ordering an assessment of HRG gene expression at a protein level in a human subject diagnosed with a locally advanced or metastatic NSCLC; and administering a treatment comprising an anti-HER3 antibody to the human subject whose HRG gene expression at a protein level is assessed as high.

(68) A method of withholding treatment of a human subject harboring a locally advanced or metastatic non-small cell lung cancer (NSCLC) tumor comprising:

ordering an assessment of HRG gene expression at a protein level in a human subject diagnosed with a locally advanced or metastatic NSCLC; and withholding a treatment comprising an anti-HER3 antibody to the human subject whose HRG gene expression at a protein level is assessed as low.

(69) A method of treating a human subject harboring a locally advanced or metastatic non-small cell lung cancer (NSCLC) tumor comprising administering a treatment comprising an anti-HER3 antibody to a human subject diagnosed with a locally advanced or metastatic NSCLC whose HRG gene expression at a protein level is assessed as high.

(70) The method of (69) in which the HRG gene expression at a protein level is assessed as high if a protein concentration value is observed, which is above a predetermined threshold, from a biological sample taken from the subject diagnosed with a locally advanced or metastatic NSCLC.

(71) The method of (70) in which the predetermined threshold is chosen statistically to minimize undesirable effects of false positives and false negatives.

(72) The method of (69) in which the predetermined threshold value is selected from the group consisting of about 0 pg/mL, about 980 pg/mL, about 1000 pg/mL, about 1622 pg/mL, about 2000 pg/mL, about 3000 pg/mL, about 4000 pg/mL, and about 5000 pg/mL.

(73) The method of (69), wherein the subject harbors wild-type EGFR.

(74) The method of (73), wherein the tumor has progressed on at least one prior systemic therapy.

(75) The method of (69), further comprising assessing gene expression at a protein level in the human subject diagnosed with the locally advanced or metastatic NSCLC, wherein HRG gene expression at a protein level is assessed using ELISA or immunohistochemistry techniques.

(76) The method of (70) in which the biological sample comprises a whole blood or serum sample.

(77) The method of (69) in which the anti-HER3 antibody is selected from the group consisting of patritumab, duligotumab (MEHD-7945A), seribantumab (MM-121), MM-111, LJM716, RG-7116, tri-specific anti-EGER/ERBB3 zybody, huHER3-8, or a derivative or fragment of any of these.

(78) The method of (69) in which the treatment comprises administering an anti-HER3 antibody in combination with one or more of (i) a HER inhibitor, (ii) a chemotherapy, (iii) radiation, and (iv) an other targeted agent,

(79) The method of (78), wherein the HER inhibitor is selected from the group consisting of trastuzumab, T-DM1, lapatinib, pertuzumab, cetuximab, panitumumab gefitinib, afatinib, dacomitinib, KU-019 and erlotinib.

(80) The method of (78), wherein the chemotherapy is selected from the group consisting of cisplatin, carboplatin, gemcitabine, pemetrexed, irinotecan, 5-fluoruracil, paclitaxel, docetaxel, and capecitabine.

(81) A method of treating a human subject harboring a locally advanced or metastatic non-small cell lung cancer (NSCLC) tumor comprising:

withholding a treatment comprising an anti-HER3 antibody from a human subject diagnosed with a locally advanced or metastatic NSCLC whose HRG gene expression at a protein level is assessed as low.

(82) The method of (81) in which the HRG gene expression at a protein level is assessed as low if a protein concentration value is observed, which is at or below a predetermined threshold, from a biological sample taken from the subject diagnosed with a locally advanced or metastatic NSCLC.

(83) The method of (82) in which the predetermined threshold is chosen statistically to minimize undesirable effects of false positives and false negatives.

(84) The method of (82) in which the predetermined threshold value is selected from the group consisting of 0 pg/mL, about 980 pg/mL, about 1000 pg/mL, about 1622 pg/mL, about 2000 pg/mL, about 3000 pg/mL, about 4000 pg/mL, and about 5000 pg/mL.

(85) The method of (81), wherein the subject harbors wild-type EGFR.

(86) The method of (85), wherein the tumor has progressed on at least one prior systemic therapy.

(87) The method of (81), further comprising assessing HRG gene expression at a protein level in the human subject diagnosed with the locally advanced or metastatic NSCLC, wherein HRG gene expression at a protein level is assessed using ELISA or immunohistochemistry techniques.

(88) The method of (82) in which the biological sample comprises a whole blood or serum sample.

(89) The method of (81) in which the treatment withheld comprises administering an anti-HER3 antibody in combination with one or more of (i) a HER inhibitor, (ii) a chemotherapy, (iii) radiation, and (iv) an other targeted agent.

(90) The method of (81) further comprising treating a human subject whose HRG gene expression at a protein level is assessed as low with a HER inhibitor selected from the group consisting of trastuzumab, T-DM1, lapatinib, pertuzumab, cetuximab, panitumumab gefitinib, afatinib, dacomitinib, KD-019 and erlotinib.

(91) The method of (81), further comprising treating a human subject whose HRG gene expression at a protein level is assessed as low with a chemotherapy selected from the group consisting of cisplatin, carboplatin, gemcitabine, pemetrexed, irinotecan, 5-fluoruracil, paclitaxel, docetaxel, and capecitabine.

(92) A method of identifying a human patient diagnosed with a locally advanced or metastatic non-small cell lung cancer (NSCLC) tumor who is likely to benefit from a treatment comprising administering an anti-HER3 antibody to the patient comprising:

obtaining a biological sample taken from a human patient diagnosed with a locally advanced or metastatic NSCLC;

using the sample, determining a value for 1-HRG gene expression at a protein level in the human patient; and optionally, recording the value determined.

(93) The method of (92), further comprising assessing if the value determined is below, at, or above a predetermined threshold value.

(94) The method of (93) in which the predetermined threshold value is selected from the group consisting of 0 pg/ML, about 980 pg/mL, about 1000 pg/mL, about 1622 about 2000 pg/mL, about 3000 pg/mL, about 4000 pg/mL, and about 5000 pg/mL.

(95) The method of (93), further comprising characterizing the HRG gene expression at a protein level as high if the value determined is above the predetermined threshold value.

(96) The method of (93), further comprising characterizing the HRG gene expression at a protein level as low if the value determined is at or below the predetermined threshold value.

(97) The method of (92), further comprising reporting the value determined to an attending physician or other medical practitioner.

(98) The method of (92) in which the sample comprises a whole blood or serum sample.

(99) The method of (92), wherein the subject does not harbor an EGFR sensitizing mutation.

(100) The method of (92), wherein the subject harbors wild-type EGFR.

(101) The method of (100), wherein the tumor has progressed on at least one prior systemic therapy.

(102) The method of (92), wherein the treatment comprises an anti-HER3 antibody in combination with one or more of (i) a HER inhibitor, (ii) a chemotherapy, (iii) radiation, and (iv) an other targeted agent.

(103) The method of any one of (69)-(102), wherein HRG gene expression is assessed as high based on randomized clinical data.

(104) A method of any of the preceding claims, wherein HRG gene expression is assessed using an regulatory authority-approved test.

(105) The method of (104), wherein the regulatory authority-approved test is an FDA (Food and Drug Administration, the United States)-approved, EMA (European Medicines agency, European Union)-approved or PMDA (Pharmaceuticals and Medical Devices Agency, Japan)-approved test.

(106) The method of (2) in which the predetermined threshold value is selected from the group consisting of 0 pg/mL, about 980 pg/mL, about 1000 pg/mL, about 1622 about 2000 pg/mL, about 3000 pg/mL, about 4000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL and about 100000 pg/mL.

(107) The method of (14) in which the predetermined threshold value is selected from the group consisting of 0 pg/mL, about 980 pg/mL, about 1000 pg/mL, about 1622 pg/mL, about 2000 pg/mL, about 3000 pg/mL, about 4000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL and about 100000 pg/mL.

(108) The method of (26) in which the predetermined threshold value is selected from the group consisting of 0 pg/mL, about 980 pg/mL, about 1000 pg/mL, about 1622 pg/mL, about 2000 pg/mL, about 3000 pg/mL, about 4000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL and about 100000 pg/mL.

(109) The method of (6) in which a tumor tissue or fragment thereof for or with which the HRG gene expression is assessed has been removed from the subject prior to any therapy.

(110) The method of (18) in which a tumor tissue or fragment thereof for or with which the HRG gene expression is assessed has been removed from the subject prior to any therapy.

(111) The method of (34) in which a tumor tissue or fragment thereof for or with which the HRG gene expression is assessed has been removed from the subject prior to any therapy.

(112) The method of (74) in which a tumor tissue or fragment thereof for or with which the HRG gene expression is assessed has been removed from the subject prior to any therapy.

(113) The method of (86) in which a tumor tissue or fragment thereof for or with which the HRG gene expression is assessed has been removed from the subject prior to any therapy.

(114) The method of (101) in which a tumor tissue or fragment thereof for or with which the HRG gene expression is assessed has been removed from the subject prior to any therapy.

for subjects from the study in Example 3 assessed as having high HRG gene expression at a protein level.

Figure 4:
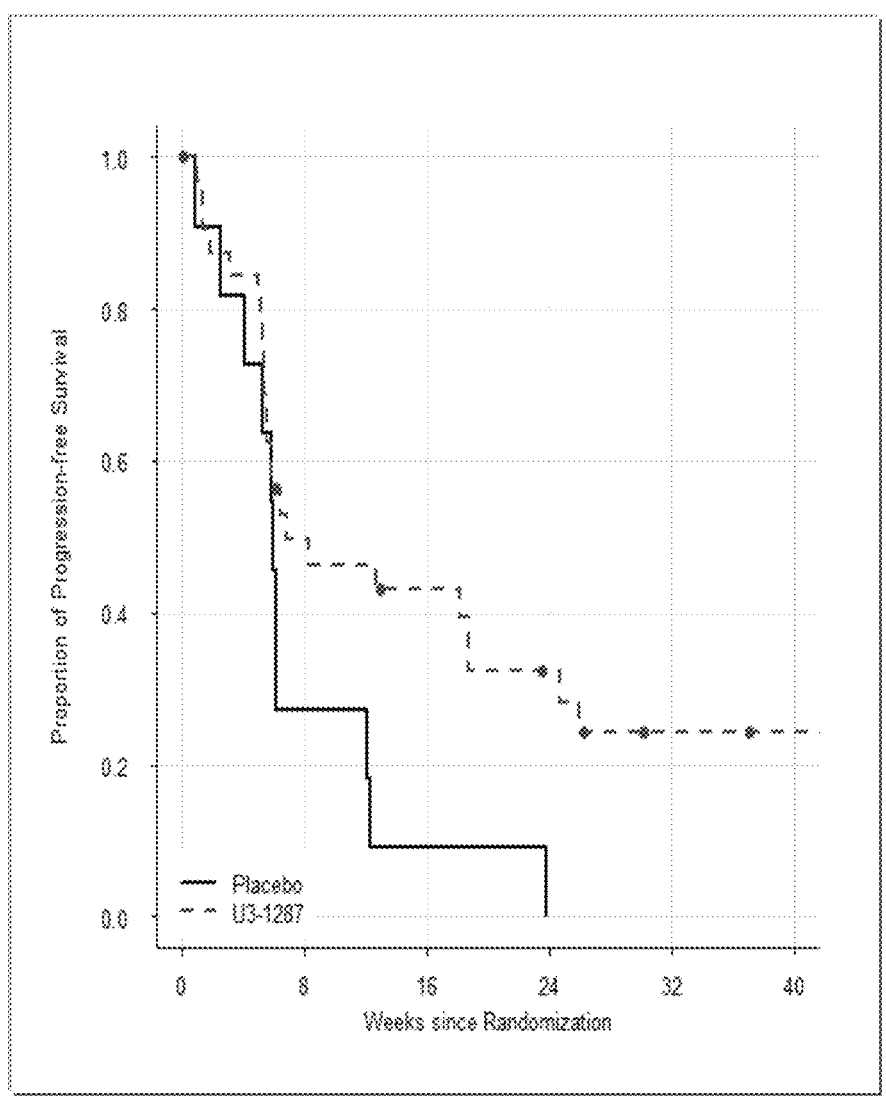

FIG. 4 depicts progression free survival (showing pooled patritumab+erlotinib vs. placebo+erlitonib) for subjects from the study in Example 3 assessed as having high HRG gene expression at a protein level.

Figure 5:
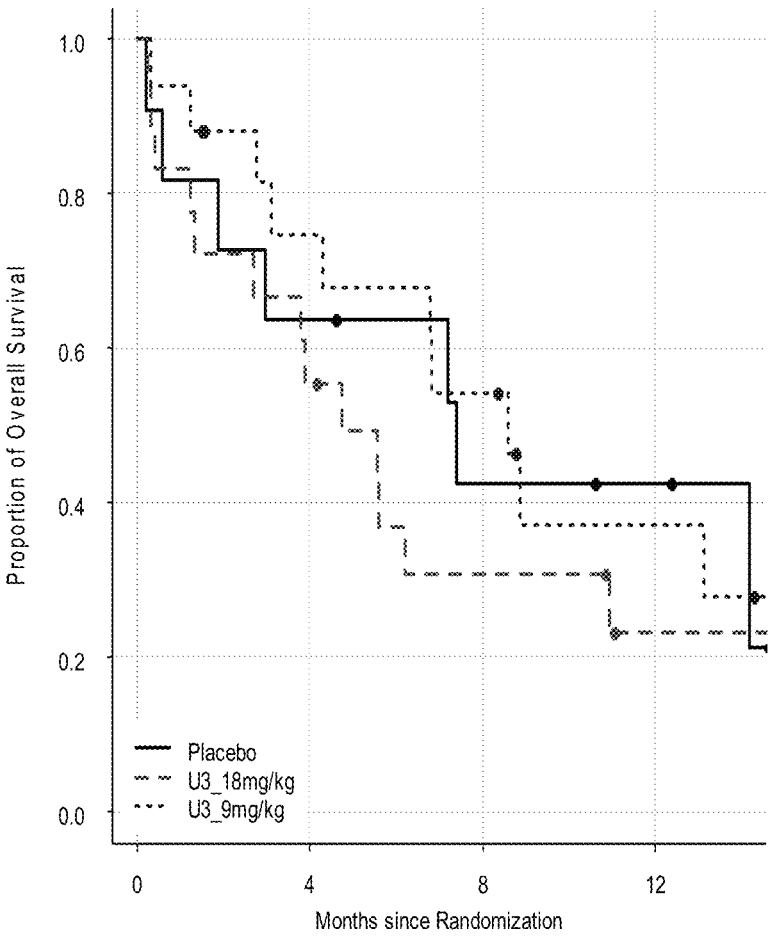

FIG. 5 depicts overall survival (showing high- and low-dose patritumab+erlotinib vs. placebo+erlitonib) for subjects from the study in Example 4 assessed as having high HRG gene expression at a protein level.

Figure 6:
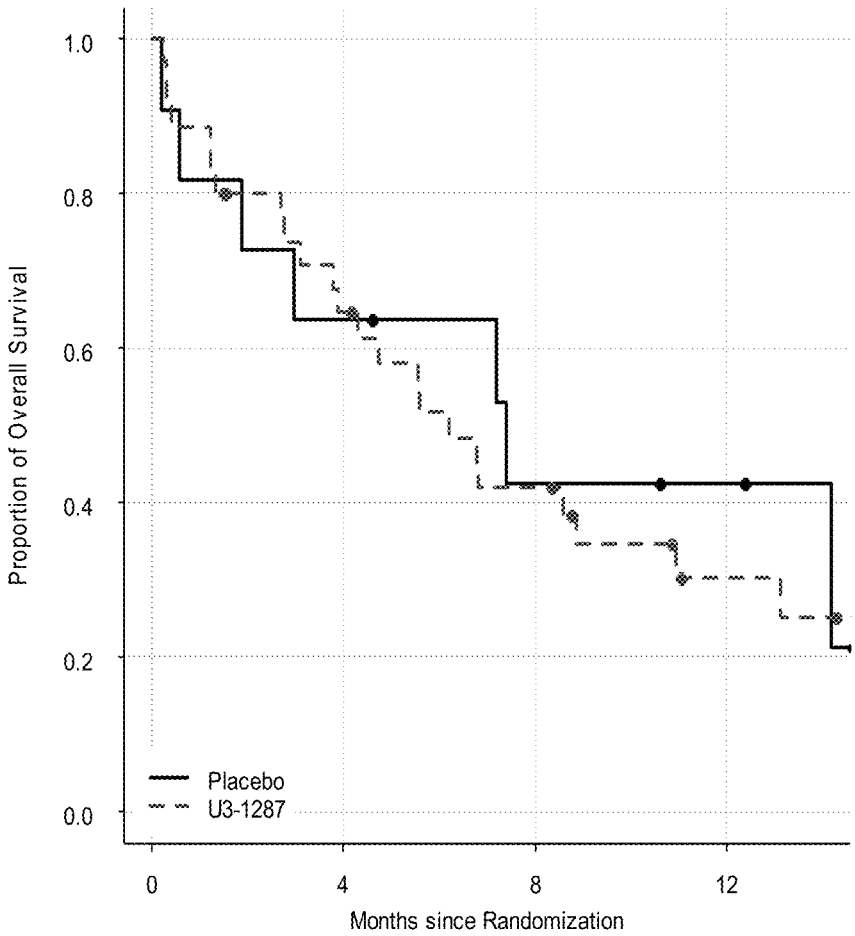

FIG. 6 depicts overall survival (showing pooled patritumab+erlotinib vs. placebo+erlitonib) for subjects from the study in Example 4 assessed as having high HRG gene expression at a protein level.

Figure 7:
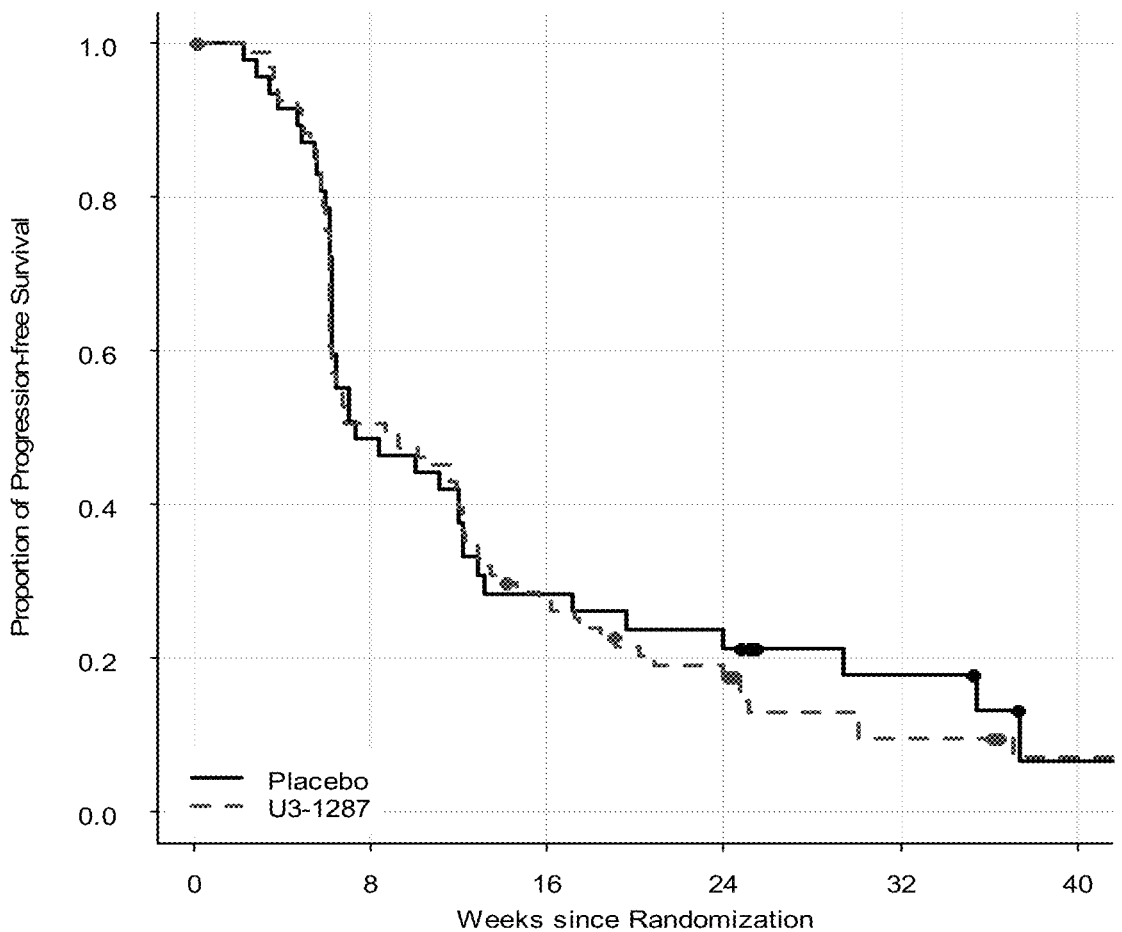

FIG. 7 depicts progression free survival (showing pooled patritumab+erlotinib vs. placebo+erlitonib) for subjects from the study in Example 5 assessed as having low HRG gene expression at a protein level.

Figure 8:
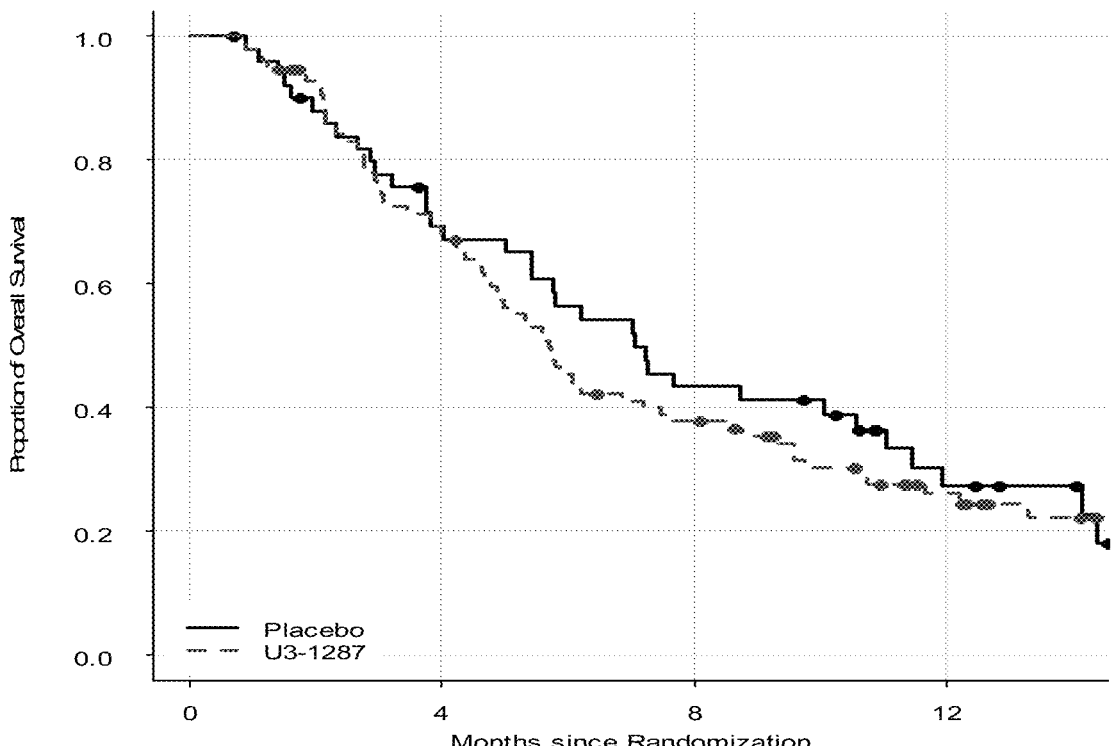

FIG. 8 depicts overall survival (showing pooled patritumab+erlotinib vs. placebo+erlitonib) for subjects from the study in Example 5 assessed as having HRG gene expression at a protein level.

Figure 9:
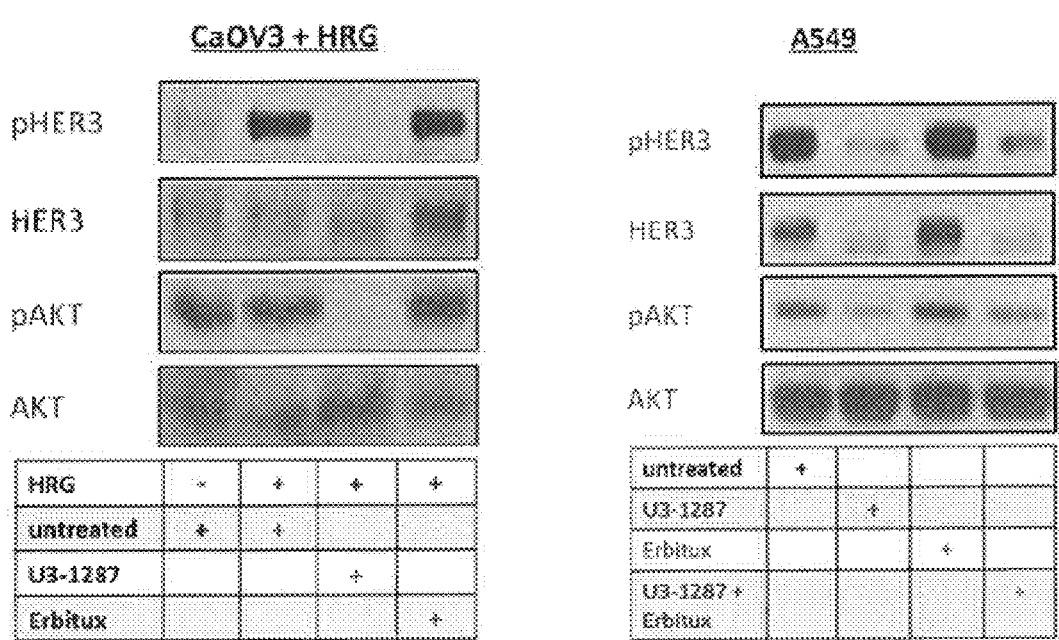

FIG. 9 depicts efficacy determined in vitro by measuring reduction of phospho-HER3 and phospho-AKT levels by Western blotting.

Figure 10:
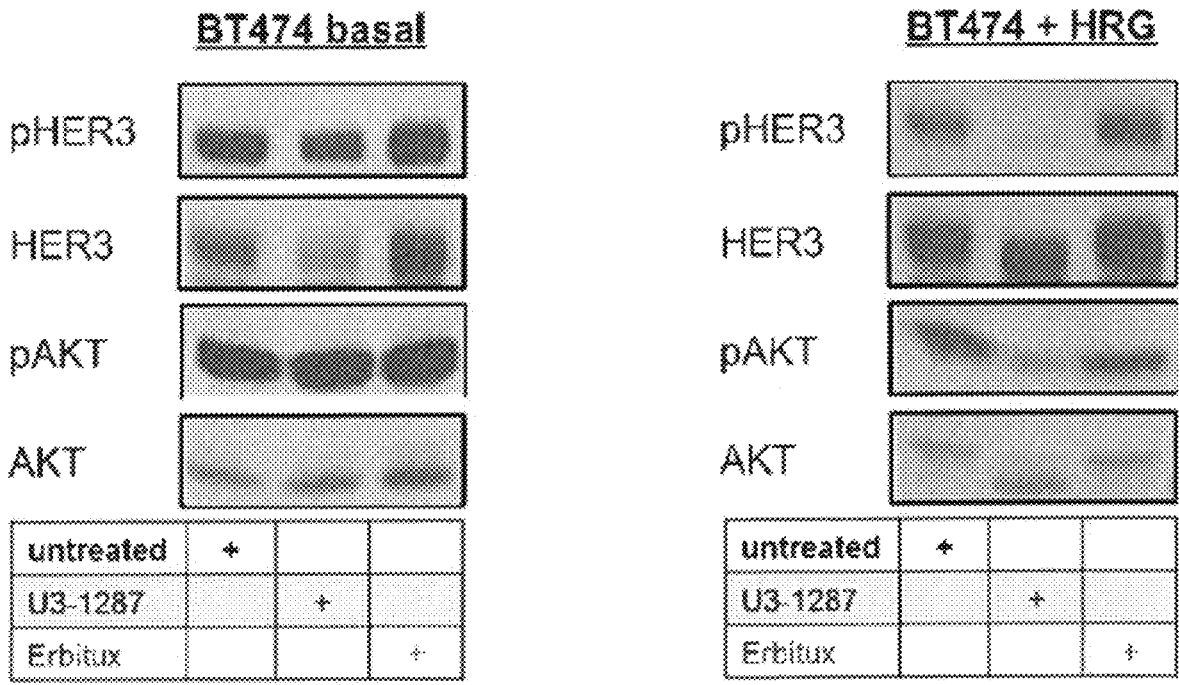

FIG. 10 depicts Western blots showing that U3-1287 can block ligand-dependent basal HER3 phosphorylation.

DETAILED DESCRIPTION OF THE INVENTION

Definitions

As used herein, unless indicated otherwise, when referring to a numerical value, the term "about" means plus or minus 10% of the enumerated value.

The term "antibody" refers to intact antibody, monoclonal or polyclonal antibodies. The antibody may be generated using recombinant DNA technologies. The antibody may originate for example, from a mouse, rat, rabbit or any other mammal. The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

As used herein, "cancer" and "tumor" are interchangeable.

As used herein, "treatment" means a medical care given to a subject or patient, or administration of a dose of a medicine. In some embodiments, "treatment" could be "pharmaceutical composition", "medicament" or "agent" that could comprise a HER inhibitor such as anti-HER3 antibody. In some embodiments, "treatment" could be a "chemotherapy, "immune therapy, "immunotherapy" or "radiotherapy".

As used herein, "EGFR mutation" means any mutation in an EGFR gene. "EGFR mutation" can be, for example, an EGFR exon 19 deletion and/or an exon 21 (L858R) substitution mutation. However, "EGFR mutation" is not limited thereto.

As used herein, "HER" is one selected from the group consisting of HER1 (EGFR), HER2, HER3 and HER4.

As used herein, "HER3" means the human protein encoded by the gene identified by Entrez Gene ID No. 2065, and allelic variants thereof.

As used herein, "HER inhibitor" means a molecule (small molecule or macromolecule, e.g., an antibody or antigen binding fragment thereof) that inhibits, neutralizes, prevents or eliminates at least a portion of the biological activity of a HER. Preferably, a HER inhibitor binds to the HER. However, "HER inhibitor" can be a molecule that does not directly bind to the HER, as long as said molecule inhibits, neutralizes, prevents or eliminates at least a portion of the biological activity of the HER. Examples of HER1 inhibitors (EGFR inhibitor) include lapatinib, erlotinib, cetuximab, gefitinib, afatinib, dacomitinib, panitumumab and KD-019. Examples of HER2 inhibitors include trastuzumab, pertuzumab and trastuzumab emtansine (T-DM1).

As used herein, "HER3 inhibitor" means a molecule (small molecule or macromolecule, e.g., an antibody or antigen binding fragment thereof) that inhibits, neutralizes, prevents or eliminates at least a portion of the biological activity of HER3. Preferably, the HER3 inhibitor binds to HER3. However, "HER3 inhibitor" can be a molecule that does not directly bind to HER3, as long as said molecule inhibits, neutralizes, prevents or eliminates at least a portion of the biological activity of HER3. The effect on "biological activity" can be direct or indirect, such as downstream signal transduction and heterodimerization with other HER family molecules such as EGFR, HER2 and HER4. For example, the HER3 inhibitor can be an inhibitor of EGFR/HER3, HER2/HER3 or HER4/HER3 heterodimerization, or an inhibitor of a signal transduction derived from any of these heterodimerizations. In this context, "HER3 inhibitor" can include, for example pertuzumab, nimotuzumab, MM-111 and cetuximab. Further, without being bound by theory it is believed that HER3 forms a heterodimer with non-HER receptors, such as MET (c-MET). Thus, in some embodiments "HER3 inhibitor" can include, for example, a MET inhibitor such as onartuzumab and/or tivantinive.

As used herein, "HRG" (also known as neuregulin-1, NRG1, heregulin, and HRG1) means the human protein encoded by the gene identified by Entrez Gene ID No. 3084, and allelic variants thereof.

As used herein, "non-small cell lung cancer" and "non-small cell lung carcinoma" are interchangeable.

As used herein, "predetermined threshold (value)" means the threshold numeric value at which a classifier gives the desirable balance between (the cost of) false negatives and false positives.

Preferably, "predetermined threshold (value)" means the potential threshold numeric value to divide the entire population (of patients or subjects) into two (or more) subgroups so that it can bring clinical benefit to patients with the threshold or higher (HRG) gene expression (used herein as "high HRG" subgroup), compared to patients with the lower (HRG) gene expression than the threshold (used herein as "low HRG" subgroup).

In case a threshold value is a dCt, preferably, "predetermined threshold (value)" means the potential threshold numeric value to divide the entire population (of patients or subjects) into two (or more) subgroups so that it can bring clinical benefit to patients with the threshold or lower value (used herein as "high HRG" subgroup), compared to patients with the higher value than the threshold (used herein as "low HRG" subgroup).

In some embodiments, "predetermined threshold" is statistically (and clinically) determined, refined, adjusted and/or confirmed through, on, or based on, a clinical study and analyses of outcome thereof (collectively, "clinical data"), and/or a preclinical or non-clinical study (collectively, "non-clinical data"), in order to minimize undesirable effects of false positives and false negatives.

In some embodiments, "predetermined threshold" is statistically (and clinically) determined, refined, adjusted and/or confirmed on, or based on, clinical data. (and optionally non-clinical data), further more preferably randomized clinical data (and optionally non-clinical data), to ensure all patients that benefit from treatment are included in the HRG high subgroup.

More preferably, "predetermined threshold" is determined, refined, adjusted and/or confirmed through, on, or based on pharmacological characteristics (i.e., mechanism of action), preclinical or non-clinical study data, clinical study data, and commercial sample data purchased from external companies or the like, in order to maximize clinical benefit from "high HRG" subgroup compared with "low HRG" subgroup, Some statistical method such as Adaptive Biomarker Threshold Design (i.e., maximum likelihood approach), Jiang W, Freidlin B, Simon R. Biomarker-Adaptive Threshold. Design: A Procedure for Evaluating Treatment With Possible Biomarker-Defined Subset Effect, J Natl Cancer Inst. 2007; 99(13):1036-43, and the like is used to determine, refine, adjust and/or confirm the threshold using the all available data of pre/non-clinical studies, clinical studies, commercial sample, etc. (to ensure all patients that benefit from treatment are included in the HRG high subgroup). In some embodiments, "predetermined threshold" is determined so that high HRG subgroup can be larger or can include all patients that drive benefit from treatment.

As used herein, "subject," "human subject," and "patient" are interchangeable.

As used herein, "subject suffering from a cancer" and "subject harboring a cancer" are interchangeable.

In some preferred embodiments, when a group of patients suffering from a cancer are treated by administering a HER3 inhibitor or placebo with or without a further medicament, and said group is divided into "high HRG" subgroup and "low HRG" subgroup using the predetermined threshold, average anti-cancer efficacy of the administered HER3 inhibitor is better than that of control (e.g. placebo) with clinical(ly) (meaningful) benefit in the "high HRG" subgroup, while average anti-cancer efficacy of the administered HER3 inhibitor is slightly better or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinically) (meaningful) benefit in "high HRG" subgroup, while average anti-cancer efficacy of the administered HER3 inhibitor is not statistically significantly better than that of control (e.g. placebo) with no clinical(ly) (meaningful) benefit in the "low HRG" subgroup.

In other preferred embodiments, when a group of patients suffering from a cancer is divided into a "high HRG" subgroup and a "low HRG" subgroup using the predetermined threshold, and each group is treated by administering a HER3 inhibitor or placebo with or without a further medicament, average anti-cancer efficacy of the administered HER3 inhibitor is better than that of a control (e.g. placebo) with clinical(ly) (meaningful) benefit in the "high HRG" subgroup, while average anti-cancer efficacy of the administered HER3 inhibitor is slightly better or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup, white average anti-cancer efficacy of the administered HER3 inhibitor is not statistically significantly better than that of control (e.g. placebo) with no clinical(ly) (meaningful) benefit in the "low HRG" subgroup.

In other embodiments, "predetermined threshold" can be the median of HRG levels which are measured in pre-/non-clinical study, clinical study and/or commercial sample, for example with a group of patients suffering from a cancer whose HRG levels are measurable (can be measured) or detectable. In other preferred embodiments, when a group of patients suffering from a cancer, such as non-small cell lung cancer (NSCLC), are treated by administering a HER3 inhibitor or placebo with or without a further medicament, and the group is divided into a high HRG subgroup and low HRG subgroup using the median HRG level of the patients as the predetermined threshold, average anti-cancer efficacy of the administered HER3 inhibitor is better than that of control (e.g. placebo) with clinical(ly) (meaningful) benefit in the "high HRG" subgroup, while average anti-cancer efficacy of the administered HER3 inhibitor is slightly betty or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup, while average anti-cancer efficacy of the administered HER3 inhibitor is not statistically significantly better than that of control (e.g. placebo) with no clinical(ly) (meaningful) benefit in the "low HRG" subgroup. In some embodiments, the predetermined threshold is the median of HRG level of a group of patients suffering from a cancer, and said threshold can be refined or adjusted (to ensure all patients that benefit from treatment are included in the HRG high sub group).

In other preferred embodiments, when a group of patients suffering from a cancer is divided into a "high HRG" subgroup and "low HRG" subgroup using the predetermined threshold, and the "high HRG" subgroup is treated by administering a HER3 inhibitor or placebo with or without a further medicament, average anti-cancer efficacy of the administered HER3 inhibitor is better than that of a control (e.g. placebo) with clinically) (meaningful) benefit in the "high HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup.

In other preferred embodiments, when "high HRG" patients suffering from a cancer are identified using the predetermined threshold, and the patients are treated by administering a HER3 inhibitor or placebo with or without a further medicament, average anti-cancer efficacy of the administered HER3 inhibitor is better than that of a control (e.g. placebo) with clinical(ly) (meaningful) benefit. In more preferred embodiments, average anti-cancer efficacy of the administered. HER3 inhibitor is statistically significantly better than that of control (e.g. placebo) with clinically) (meaningful) benefit.

As used herein, "further medicament" means any therapeutic or prophylactic molecule other than the HER3 inhibitor which is to be used in combination with said molecule. In some embodiments, "further medicament" is one or more of a HER inhibitor, a chemotherapy, or a radiation therapy.

In some embodiments, an indicator (index) of "anti-cancer efficacy" can be progression-free survival (PFS) or overall survival (OS), but is not limited thereto. The indicator can be any surrogate marker of anti-cancer efficacy of a HER3 inhibitor.

As used herein, "high HRG" is a numerical value representing, or represents, a level of HRG gene expression at or above a predetermined threshold. In the present invention, "high HRG", "high HRG (sub)group" and "high HRG patient (or subject)" mean a level of HRG gene expression at or above a (predetermined) threshold, (sub)group having level(s) of HRG gene expression at or above a (predetermined) threshold, and, patient (or subject) having a level of HRG gene expression at or above a (predetermined) threshold, respectively. The HRG classification can be based on HRG gene expression at a protein level, for example.

As used herein, "low HRG" is a numerical value representing, or represents, a level of HRG gene expression at or below a predetermined threshold. In the present invention, "low HRG", "low HRG (sub)group" and "low HRG patient (or subject)" mean a level of HRG gene expression at or below a (predetermined) threshold, (sub)group having level(s) of HRG gene expression at or below a (predetermined) threshold, and, patient (or subject) having a level of HRG gene expression at or below a (predetermined) threshold, respectively. The HRG classification can be based on HRG gene expression at a protein level, for example.

As used herein, "response" or "responding" to treatment means, with regard to a treated tumor, that the tumor displays: (a) slowing of growth, (b) cessation of growth, or (c) regression.

The methods disclosed herein can be used for identifying a subject, for example a human subject, harboring or diagnosed with a tumor or cancer cells. In some embodiments, the subject harbors solid or liquid tumors that may be driven by the HER3 pathway, or that may have resistance to other therapies mediated by the HER3 pathway. In some embodiments, the subject harbors lung cancer, colorectal cancer, head and neck cancer, breast cancer, gastrointestinal cancer, pancreatic cancer, prostate cancer, ovarian cancer, endometrial cancer, salivary gland cancer, renal cancer, colon cancer, gastric cancer (stomach cancer), thyroid cancer, bladder cancer, glioma, melanoma, metastatic breast cancer, epidermal carcinoma, esophageal cancer, cervical cancer, squamous cell carcinoma, small-cell lung cancer, or non-small cell lung cancer. In some embodiments, the methods disclosed herein can be used to identify a subject harboring a locally advanced or metastatic tumor, such as a locally advanced or metastatic NSCLC (tumor) or locally advanced or metastatic head and neck cancer. In some embodiments, methods disclosed herein can be used to identify a subject, such as a subject harboring a locally advanced or metastatic NSCLC (tumor), that is likely to benefit from a treatment comprising an anti-HER3 antibody or HER3 inhibitor having a low molecular weight. In some embodiments, the subject is harboring a Stage III, e.g., Stage IIIb, or Stage IV tumor. Methods of identifying a subject can comprise, for example, assessing HRG gene expression at a protein level in a human subject diagnosed with a tumor or cancer.

In some embodiments, methods disclosed herein can be used to identify, a subject harboring a locally advanced or metastatic NSCLC (tumor), that is likely to benefit from a treatment comprising (administering) an anti-HER3 antibody or HER3 inhibitor having a low molecular weight, provided that, any subject who having an ALK gene fusion or rearrangement is excluded from those to whom the methods are applied.

In some embodiments, the methods disclosed herein can be used to treat a subject identified as harboring a tumor or cancer cells. In some embodiments, methods of identifying or treating a human subject harboring a locally advanced or metastatic NSCLC (tumor) can comprise assessing HRG gene expression at a protein level in a human subject diagnosed with a locally advanced or metastatic NSCLC. In some embodiments, the subject does not harbor an epidermal growth factor receptor (EGFR) sensitizing mutation. In some embodiments, the subject harbors wild-type EGFR. In some embodiments, the subject does not harbor an ALK gene fusion or rearrangement. In some embodiments, the disease or tumor has progressed on at least one prior systemic therapy, such as chemotherapy, Some embodiments comprise administering a treatment comprising an anti-HER3 antibody to a human subject whose HRG gene expression at a protein level is assessed as high. In some embodiments, treatment comprises (administering) an anti-HER3 antibody in combination with at least one agent that inhibits a HER family receptor other than HER3. In some embodiments, treatment comprises administering an anti-HER3 antibody in combination with at least one agent that inhibits a non-HER family tyrosine kinase receptor. In some embodiments, an anti-HER3 antibody is administered in combination with non-specific chemotherapy.

In some preferred embodiments, patients to whom the methods disclosed herein can be applied are heregulin high, EGFR wild-type subjects with locally advanced or metastatic non-small cell lung cancer who have progressed on at least one prior systemic therapy. In some embodiments, the patients are HER inhibitor naïve. In preferred embodiments, a tumor tissue or fragment thereof for or with which the HRG gene expression is assessed has been removed from the subject or patient prior to any (systemic) therapy.

In some preferred embodiments, patients to whom the methods disclosed herein can be applied include a subject with a first-line metastatic or locally advanced head and neck cancer that will be concurrently treated with one or more of cetuximab, cisplatin, panitumumab, 5-fluoruracil, radiotherapy, and radiation therapy (locally advanced only).

In some embodiments, patients to whom the methods disclosed herein can be applied include a subject with a second-line metastatic NSCLC or other cancer that will be concurrently treated with docataxel.

In some embodiments, patients to whom the methods disclosed herein can be applied include a subject with a NSCLC or other cancer that will be concurrently treated with an immune therapy.

In some embodiments, patients to whom the methods disclosed herein can be applied include a subject with a third line, HER2 positive, (metastatic) breast cancer that will be concurrently treated with a PI3K pathway inhibitor.

In some embodiments, patients to whom the methods disclosed herein can be applied include a subject with HER2 negative (metastatic) breast cancer that will be concurrently treated with a hormone therapy or PI3K pathway inhibitor.

In the present invention, PI3K pathway inhibitors include PI3K inhibitors, mTOR inhibitors and AKT inhibitors.

In some embodiments, patients to whom the methods disclosed herein can be applied include a subject with a first-line metastatic EGFR-sensitizing mutant positive for NSCLC or other cancer that will be concurrently treated with one or more of erlotinib, gefitini, and afitinib.

In some embodiments, patients to whom the methods disclosed herein can be applied include a subject with a first-line metastatic NSCLC or other cancer that will be concurrently treated with platinum-based chemotherapy.

In some embodiments, patients to whom the methods disclosed herein can be applied include a subject with RAS wild-type colorectal cancer that will be concurrently treated with one or more of cetuximab, panitumumab, and chemotherapy.

In some embodiments, patients to whom the methods disclosed herein can be applied include a subject that with HER2 positive first line metastatic breast cancer or other cancer that will be concurrently treated with one or more of trastuzumab, paclitaxel, docataxel, TDM1 and pertuzumab.

In some embodiments, patients to whom the methods disclosed herein can be applied include a subject that with HER2 positive second or later line metastatic breast cancer or other cancer that will be concurrently treated with one or more of lapatinib, capecitabine, trastuzumab, and paclitaxel.

In some embodiments, patients to whom the methods disclosed herein can be applied have not failed with an earlier line of therapy. In some embodiments, patients to whom the methods disclosed herein can be applied have not failed with an earlier line of therapy and the patients have been classified as "high HRG."

In some embodiments, the methods disclosed herein can be used to identify and/or treat HRG high, EGFR wild-type subjects with locally advanced or metastatic NSCLC who will benefit from treatment of patritumab in combination with a HER inhibitor.

In some embodiments, the methods disclosed herein can be used to identify and/or treat HRG high, EGFR wild-type subjects with locally advanced or metastatic NSCLC who will benefit from treatment of patritumab in combination with chemotherapy.

In some embodiments, the methods disclosed herein can be used to identify and/or treat HRG high, EGFR mutated subjects, for example with locally advanced or metastatic NSCLC who will benefit from treatment of patritumab in combination with a HER inhibitor.

In some embodiments, the methods disclosed herein can be used to identify and/or treat HRG high, EGFR mutated subjects with locally advanced or metastatic NSCLC who will benefit from treatment of patritumab in combination with chemotherapy.

In some embodiments, the methods disclosed herein can be used to identify and/or treat a "HRG high" patient suffering from a cancer who will benefit from treatment of patritumab in combination with an immune therapy or immunotherapy. Such cancers include NSCLC.

In some embodiments, the methods disclosed herein can be used to identify and/or treat a "HRG high" patient suffering from a cancer who will benefit from treatment of patritumab in combination with a hormone therapy or PI3K (phosphoinositide 3-kinase) pathway inhibitor. Such cancers include breast cancer, preferably, HER2-negative breast cancer. Such PI3K pathway inhibitors include PI3K inhibitors, AKT inhibitors and mTOR (mammalian Target Of Rapamycin) inhibitors.

In some embodiments, the methods disclosed herein can be used to identify and/or treat a "HRG high" patient suffering from a cancer who will benefit from treatment of patritumab in combination with a PI3K inhibitor. Such cancers include breast cancer, preferably, HER2-positive breast cancer.

In some embodiments, the methods disclosed herein can be used to identify and/or treat a "HRG high" patient suffering from a cancer who will benefit from treatment of patritumab in combination with a ALK inhibitor. Such cancers include NSCLC. Such ALK (anaplastic lymphoma kinase) inhibitor includes crizotinib (Xalkori).

In some embodiments, the methods disclosed herein can be used to identify and/or treat acute respiratory distress syndrome, pulmonary fibrosis, schizophrenia, heart disease, atherosclerosis, and Duchenne's muscular dystrophy.

HER3 Antibodies

Antibodies suitable for treatment are not particularly limited, and can be any protein or ligand that can bind to HER3. In some embodiments, the antibodies can be binding proteins or fragments thereof that bind to HER3. In some preferred embodiments, the antibodies can inhibit, neutralize, prevent or eliminate at least a portion of the biological activity of HER3.

HER3 antibodies can be, for example, one or more of patritumab, duligotumab (MEHD-7945A), seribantumab (MM-121), MM-111, LJM716, RG-7116 (glycoengineered anti-HER3 monoclonal antibody), tri-specific anti-EGFR/ERBB3 zybody, huHER3-8 or a derivative or fragment of any of these that can bind to HER3.

Antibody fragments include, for example, Fab fragments, Fab' fragments, F(ab')$_2$ fragments, Fv fragments, diabodies (Hollinger et al. (1993) *Proc. Natl. Acad. Sci. U.S.A.* 90:6444-6448), single chain antibody molecules (Plückthum in: *The Pharmacology of Monoclonal Antibodies* 113, Rosenburg and Moore, eds., Springer Verlag, N.Y. (1994), 269-315), scFv fragments, and other fragments that can inhibit HER3.

Derivatives of antibodies or antibody fragments can include, for example, a bispecific antibody, a multispecific antibody, a biscFv fragment, a diabody, a nanobody, an antibody-drug conjugate, an immunotoxin, and/or an immunocytokine, but are not limited thereto.

Further examples of suitable antibodies can be found, for example, in U.S. Pat. No. 7,705,130, which is herein incorporated by reference in its entirety.

According to the present invention, an isolated binding protein that is capable of binding to HER3 interacts with at least one epitope in the extracellular part of HER3. The epitopes are preferably located in domain which is the amino terminal domain, in domain S1 and S2, which are the two Cysteine-rich domains, or in domain L2, which is flanked by the two Cysteine-rich domains. The epitopes may also be located in combinations of domains such as but not limited to an epitope comprised by parts of L1 and S1.

Biological Sample

A biological sample taken from a subject, such as a subject diagnosed with a locally advanced or metastatic NSCLC, can be used as a source of protein or a source of thin sections for immunohistochemistry (IHC), so the level of HRG gene expression in the sample can be determined. The biological sample can comprise, for example, blood, e.g., whole blood, or blood derivatives including exosomes, serum, plasma, tissue, cells, and/or circulating tumor cells. In some embodiments, the biological sample can be taken from a tumor.

The biological sample can be obtained by any known methods, such as venipuncture or with conventional tumor biopsy instruments and procedures. Endoscopic biopsy, excisional biopsy, incisional biopsy, fine needle, biopsy, punch biopsy, shave biopsy and skin biopsy are examples of recognized medical procedures that can be used by one of skill in the art to obtain tumor samples. The biological sample should be large enough to provide sufficient protein or thin sections for measuring HRG gene expression.

In some embodiments, the methods described herein comprise providing an autologous tissue sample or consenting to the taking of an autologous tissue sample, e.g., to facilitate an assessment of HRG gene expression at a protein level in a human subject diagnosed with a locally advanced or metastatic NSCLC.

The biological sample can be in any form that allows measurement of HRG expression or content. In other words, the sample must be sufficient for protein extraction or preparation of thin sections. Accordingly, the sample can be fresh, preserved through suitable cryogenic techniques, or preserved through non-cryogenic techniques. For example, a standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

HRG Gene Expression

As described herein, determining or measuring the level of HRG gene expression in a biological sample can be performed by any suitable method. Several such methods are known in the art. For example, determining HRG gene expression can be done by measuring the level or amount of HRG protein in a sample.

HRG is produced in numerous isoforms upon expression of the HRG gene. Without being bound by theory, it is believed that the EGF-like domain of HRG is essential for binding to HER3. Therefore, when determining the level of HRG gene expression as described herein, the HRG assay preferably can be, for example designed to detect at least the EGF-like domain of HRG, in order to detect most, if not all, of the HRG isoforms present. If an anti-HRG antibody is used to detect HRG protein, the antibody can recognize the EGF-like domain. In some embodiments, however, the anti-HRG antibody used to detect HRG protein does not recognize the EGF-like domain.

HRG gene expression can be detected by any known methods. Non-limiting examples of suitable detection methods for measuring the level of HRG gene expression at the protein level include enzyme linked immunosorbent assay (ELISA) and IHC analysis.

ELISA

Performing an HRG ELISA requires at least one antibody against HRG, e.g., a detection antibody. HRG protein from a sample to be analyzed can be immobilized on a solid support such as a polystyrene microliter plate. This immobilization can be by non-specific binding, e.g., through adsorption to the surface. Alternatively, immobilization can be by specific binding, e.g., through binding of HRG from the sample by a capture antibody in a "sandwich" ELISA. After the HRG is immobilized, the detection antibody can be added, and the detection antibody can form a complex with the bound HRG. The detection antibody can be linked to an enzyme, either directly or indirectly, e.g., through a secondary antibody that specifically recognizes the detection antibody. Between each step, the plate, with bound. HRG, can be washed with a mild detergent solution. Typical ELISA protocols can include one or more blocking steps, which involve use of a non-specifically-binding protein such as bovine serum albumin to block unwanted non-specific binding of protein reagents to the plate. After a final wash step, the plate can be developed by addition of an appropriate enzyme substrate to produce a visible signal that indicates the quantity of HRG in the sample. The substrate can be, e.g., a chromogenic substrate or a fluorogenic substrate. ELISA methods, reagents and equipment are well-known in the art and commercially available.

Some embodiments of performing an ELISA are described below. The disclosed methods provide for accurate results when performing an ELISA on a variety of sample types, including biological samples that contain high amounts of multiple different proteins (e.g., samples such as plasma and serum). In one aspect, the disclosed ELISA method may be performed to detect natural and/or recombinant human Heregulin (HRG).

The ELISA methods disclosed herein comprise sequential steps of contacting a solid surface with a plurality of solutions each comprising in turn a capture antibody, a blocking agent, a sample suspected of containing an analyte, a detection antibody and an enzyme conjugate, in which the solid surface is subjected to a wash process after each sequential step, the wash process comprising:

(a) cycling wash buffer on and off the solid surface at a rapid rate until bubbles are observed at which point the cycled wash buffer is removed;

(b) optionally repeating step (a) using fresh wash buffer; and (c) rinsing the solid surface with fresh wash buffer;

provided that after completing the wash process following the enzyme conjugate sequential step, the solid surface is contacted with a solution comprising an enzyme substrate.

The cycling of wash buffer may comprise applying and aspirating the wash buffer on and off the solid surface quickly and repeatedly using a "piston" action. The "piston" action may be performed by repeatedly pumping the plunger end of a pipette (such as, for example, an air displacement pipette, a positive displacement pipette or a multichannel pipettor) to move the wash buffer in and out of an associated pipette tip. Alternatively, the bulbous end of a transfer pipette or a Pasteur pipette can be repeatedly squeezed and released to carry out the piston action. Other comparable means of dispensing and removing wash buffer may be employed.

Not to be bound by theory, it is believed that such a piston action effectively exposes non-specifically adsorbed proteins to the wash buffer, effectively removing the proteins. The wash buffer is cycled on an off the solid surface until bubbles are observed, indicating sufficient washing of the solid surface has occurred. In some embodiments, the wash buffer is cycled 10 to 30 times on and off the solid surface. In some embodiments the wash buffer is cycled about 20 times on and off the solid surface. In some embodiments, the wash buffer is cycled at least 10, at least 20, or at least 30 times on and off of the solid surface.

In some embodiments, the cycling step (a) is performed one to two, three or four times before performing the rinsing step (c). In a specific embodiment, the cycling step (a) is performed two times before performing the rinsing step (c). In some embodiments, the cycling step (a) is performed at least two times before performing the rinse step (c).

The rinsing step involves applying and removing wash buffer to and from the solid surface. The rinsing step may involve a standard "fill and aspirate" methodology whereby the solid surface is contacted one time with wash buffer which is then immediately removed via aspiration. Alternatively, the wash buffer may be removed by decantation. The rinsing step is conducted to ensure that no bubbles remain on the solid surface. Accordingly, in some embodiments the rinsing step does not involve performing multiples cycles or a pistoning action. If the solid surface contains wells or raised edges, the surface may be inverted and blotted on a dry, flat, absorbent surface after removing the wash buffer to ensure all wash buffer is removed.

ELISA Solid Surfaces

In some embodiments, the ELISA method disclosed herein is performed on a solid surface that is a cell culture plate comprising one or more wells. An exemplary solid surface for use in the disclosed ELISA methods is a microlitre plate (also known as a microplate or microwell plate). Suitable plates may be made of a polystyrene, polycarbonate or polypropylene. In a specific embodiment, the ELISA is performed using a 96-well microplate.

ELISA Solutions Comprising a Capture Antibody

The disclosed ELISA methods involve contacting a solid surface with a solution comprising a capture antibody. The capture antibody may be a monoclonal or a polyclonal antibody and recognizes an antigen of interest that is the analyte to be detected in the ELISA. In some embodiments, the capture antibody is mouse antibody raised against a specific human protein or peptide. In a specific embodiment the capture antibody is a mouse anti-human HRC antibody.

The solution comprising a capture antibody may comprise the antibody reconstituted with phosphate buffered saline (PBS). In some embodiments, the solution may contain about 1.5 to about 5.0 ug/mL antibody. In a specific embodiment the solution contains about 4.0 ug/mL antibody in PBS.

In some embodiments, the solid surface may be incubated with the solution comprising a capture antibody for at least 4 hours at a temperature of about 65° to about 80° F. In some embodiments the solid surface is incubated with the solution for about 8 hours or overnight at about 70° F. In a specific embodiment, the solid surface is covered and/or sealed while in contact with the capture antibody solution.

ELISA Solutions Containing a Blocking Agent

The solid surface is blocked by adding a solution containing a blocking agent. In some embodiments, the blocking agent solution comprises about 1% bovine serum albumin (BSA) in PBS at a pH between about 7.2 and about 7.4. In some embodiments the blocking agent solution contains less than less than about 0.5% proteases.

The solid surface may be incubated with the blocking agent solution for at least one hour. In some embodiments, the solid surface is incubated with the blocking agent solution at about 70° F.

ELISA Sample Solutions

The solution comprising a sample suspected of containing an analyte may consist of an undiluted biological sample or it may comprise a biological sample diluted with a solution such as, for example, PBS. In a specific embodiment, the sample solution consists of undiluted serum or plasma and the serum or plasma is contacted directly with the solid surface.

The analyte may be, for example, an antigen such as a protein or peptide. In a specific embodiment, the analyte is a growth factor such as HRG or, specifically, soluble HRG.

The solid surface may be incubated with the sample solution for about 2 hours or longer at about 70° F. In a specific embodiment, the solid surface is covered and/or sealed during incubation with the sample solution.

ELISA Solutions Containing a Detection Antibody

A detection antibody is an antibody that recognizes an antigen of interest that is the analyte being detected in the ELISA. As such, the capture antibody and the detection antibody both recognize the same antigen. However, these two antibodies may not recognize the same region or epitope of the antigen. The detection antibody may a monoclonal antibody or a polyclonal antibody. In some embodiments, the detection antibody is goat antibody raised against a specific human protein or peptide. In a specific embodiment the capture antibody is a goat anti-human HRG antibody.

The solution comprising a detection antibody may comprise the antibody reconstituted with phosphate buffered saline (PBS) or BSA solution. In some embodiments, the solution may contain from about 100 to about 200 ng/mL antibody in a solution of 1% BSA in PBS, pH 7.2-7.4. In a specific embodiment the solution contains about 150 ng/mL in a solution of 1% BSA in PBS, pH 7.2-7.4. In some embodiments, the detection antibody solution does not contain normal goat serum.

The detection antibody is conjugated with a detection agent such as, for example, biotin. Such a detection agent permits binding of the detection antibody to an enzyme/substrate detection system such as, for example, an avidin or streptavidin linked enzyme. In a specific embodiment, the detection antibody is biotinylated anti-human HRG antibody.

In some embodiments, the solid surface is incubated with the detection antibody solution for at least 1.5, 2 or 3 hours at a temperature of about 70° F. In some embodiments, the solid surface is covered and/or sealed while in contact with the detection antibody solution.

ELISA Solutions Containing an Enzyme Conjugate

The disclosed ELISA methods involve contacting the solid surface with an enzyme conjugate comprising a binding agent coupled to a reporter enzyme such as alkaline phosphatase (AP) or horseradish peroxidase (HRP). The binding agent binds to the detection agent that is conjugated to the detection antibody. Streptavidin is an exemplary binding agent that binds to a biotinylated antibody. The reporter enzyme converts a colorless substrate to a detectable, colored product. An exemplary enzyme is horse radish peroxidase (HRP), which converts a hydrogen peroxide/tetramethylbenzidine substrate mixture to a detectable chromogen. In some embodiments, the enzyme conjugate employed in the ELISA is streptavidin-horse radish peroxidase (HRP).

In some embodiments, the enzyme conjugate solution comprises the enzyme conjugate diluted in a solution of 1% BSA in PBS, pH 7.2-7.4. In some embodiments the solid surface may be incubated with the enzyme conjugate solution for about 20 minutes at about 70° F. and away from direct light. The solid surface may be covered and/or sealed during incubation.

ELISA Solutions Comprising an Enzyme Substrate

After completing the wash process following the enzyme conjugate sequential step, the solid surface is contacted with a solution comprising an enzyme substrate. Suitable substrates include colorless products that are converted to colored products upon exposure to the enzyme linked to the binding agent of the enzyme conjugate. Upon conversion from a colorless product to a colored product, the optical density of the enzyme substrate solution on the solid surface can be measured on an ELISA plate reader at target wavelengths.

Exemplary, suitable enzyme substrates include Nitroblue Tetrazolium (NBT) with the 5-Bromo-4-Chloro-3-Indolyl Phosphate (BCIP) (alkaline phosphatase substrate), Fast Red TR/Naphthol AS-MX with 4-Chloro-2-methylbenzenediazonium/3-Hydroxy-2-naphthoic acid 2,4-dimethylanilide phosphate (alkalai phosphate substrate) and a 1:1 mixture of hydrogen peroxide ($H_2O_2$) and tetramethylbenzidine (HRP substrate mixture).

In some embodiments, the enzyme substrate solution is incubated with the solid surface for at least 20 minutes at about 70° F., away from direct light.

ELISA Wash Buffer

The solid surface is washed after contacting with each of the capture antibody, blocking agent, sample, detection antibody and enzyme conjugate solutions. Wash buffer contains a surfactant, such as a polysorbate surfactant. A specific suitable surfactant is polyethylene glycol sorbitan monolaurate (e.g., TWEEN® 20, Sigma Aldrich, Missouri, USA). The surfactant may be present in, for example, PBS pH 7.2-7.4 or Tris Buffered Saline, pH 8.0. In a specific embodiment, the wash buffer comprises 0.05% polyethylene glycol sorbitan monolaurate in PBS, pH 7.2-7.4.

The solid surface of the ELISA may be contacted with a stop solution after incubation with the enzyme substrate solution is complete. In some embodiments, the stop solution comprises 2-NH$_2$SO$_4$. The stop solution may be thoroughly mixed with the existing solution on the plate after added.

The optical density of the ELISA solid surface may be determined by a spectrophotometric reading after the solid surface is contacted with the stop solution. In some embodiments, the optical density is determined immediately upon addition of the stop solution.

In one embodiment of the disclosed ELISA methods, the method is performed with a DuoELISA Development kit or detecting human NRG1-b1/HRG1-b1 (R&D Systems, Inc., Minneapolis, USA; catalog number DY377).

Immunohistochemistry

The presence and level of HRG in a sample can be determined by immunohistochemistry (IHC) or immunofluorescence (IF). Assaying HRG by IHC or IF requires at least one antibody against HRG. Anti-HRG antibodies suitable for IHC and are commercially available. For example, suitable antibodies can be purchased from R&D Systems (Minneapolis, MN), abeam (Cambridge, MA), Santa Cruz Biotechnology, Inc. (Santa Cruz, CA), or Novus Biologicals (Littleton, CO). Using standard techniques, the anti-HRG antibody can be used to detect the presence of HRG protein in thin sections, e.g., 5 micron sections, obtained from tumors, including FFPE sections and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-HRG detection antibody. The presence of HRG protein is then detected by binding of the anti-HRG antibody (primary antibody) to the HRG protein. The detection antibody (secondary antibody), which recognizes and binds to the primary antibody, is linked to a detectable enzyme or fluorophore. Typically, the tumor sections are washed and blocked with non-specific protein such as bovine serum albumin between steps. If the detection antibody is linked to a detectable enzyme, the slide is developed using an appropriate enzyme substrate to produce a visible signal. If the detection antibody is linked to a fluorophore, the slide is viewed by using a fluorescence microscope. The samples can be counterstained with, for example, hematoxylin.

Assessing HRG Gene Expression

HRG gene expression can be assessed in a biological sample from a human patient, such as a biological sample obtained from, taken from, or received from a human patient. Some embodiments comprise ordering or receiving an assessment of HRG gene expression at a protein level. Some embodiments comprise determining a value for HRG gene expression at a protein level and, optionally, recording the value determined.

In some embodiments, HRG expression at a protein level is assessed using a regulatory authority-approved test. In some embodiments, the regulatory authority-approved test is an FDA-approved test, an EMA-approved test, or a JPMA-approved test.

HRG Gene Expression levels can be interpreted with respect to a predetermined threshold. An HRG gene expression level that is equal to or higher than the threshold score can be interpreted as predictive of the likelihood that a subject would respond to treatment with a HER3 inhibitor, e.g., an anti-HER3 antibody. In some embodiments, HRG gene expression levels lower than the threshold score can be interpreted as predictive of a tumor being resistant (non-responsive) to treatment with a HER3 inhibitor.

In some embodiments, HRG gene expression can be assessed as "high HRG" or "low HRG" based on a numerical value representing the level of HRG gene expression in a biological sample. A subject can be assessed as high HRG or low HRG based on, for example, HRG expression at a protein level. The expression level can be assessed by any known methods, such as those described above.

For example, HRG gene expression at a protein level can be assessed as "high HRG" if a protein concentration value is observed, which is at or above a predetermined threshold, from a biological sample. In some embodiments, the predetermined threshold is chosen statistically to minimize undesirable effects of false positives and false negatives and can be, for example, 0 pg/mL, about 980 pg/mL, about 1000 pg/mL, about 1622 pg/mL, about 2000 pg/mL, about 3000 pg/mL, about 4000 pg/mL, about 5000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL or about 100000 pg/mL. In some embodiments, HRG expression can be assessed as "high HRG" if the protein concentration value in the biological sample is more than: about 0 pg/mL, about 980 pg/mL, about 1000 pg/mL, about 1622 pg/mL, about 2000 pg/mL, about 3000 pg/mL, about 4000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL or about 100000 pg/mL. In some embodiments, the HRG expression is assessed as "low HRG" if the protein concentration value is less than: about 980 pg/mL, about 1000 pg/mL, about 1622 pg/mL, about 2000 pg/mL, about 3000 pg/mL, about 4000 pg/mL, about 5000 pg/mL, about 6000 pg/mL, about 7000 pg/mL, about 8000 pg/mL, about 9000 pg/mL, about 10000 pg/mL, about 11000 pg/mL, about 12000 pg/mL, about 13000 pg/mL, about 14000 pg/mL, about 15000 pg/mL, about 16000 pg/mL, about 17000 pg/mL, about 18000 pg/mL, about 19000 pg/mL, about 20000 pg/mL, about 22000 pg/mL, about 24000 pg/mL, about 26000 pg/mL, about 28000 pg/mL, about 30000 pg/mL, about 35000 pg/mL, about 40000 pg/mL, about 50000 pg/mL, about 60000 pg/mL, about 70000 pg/mL, about 80000 pg/mL, about 90000 pg/mL or about 100000 pg/mL.

In some embodiments, the HRG gene expression at a protein level can be assessed based on soluble HRG that can originate from one or more sources. For example, in some embodiments HRG gene expression at a protein level can originate from both normal and tumor cells.

In some embodiments, higher HRG gene expression is correlated with better hazard ratios and p-values.

Treatment

In some embodiments, the subject can be treated by administering a treatment comprising anti-HER3 antibody to a subject suffering from a cancer or other disease with HRG gene expression assessed as high. In some embodiments, the subject can be treated by withholding a treatment comprising an anti-HER3 antibody from a subject suffering from a cancer or other disease with HRCT gene expression assessed as low.

In some embodiments, the subject can be treated by receiving or undergoing a treatment comprising an anti-HER3 antibody if HRG gene expression at a protein level is assessed as high or abstaining from a treatment comprising an anti-HER3 antibody if HRG gene expression at a protein level is assessed as low.

In some embodiments, the subject can be treated by electing to withhold or abstain from a treatment comprising an anti-HER3 antibody if HRG gene expression at a protein level is assessed as low or electing to administer a treatment comprising an anti-HER3 antibody if HRG gene expression at a protein level is assessed as high.

The anti-HER3 antibody can be any protein or ligand that can bind to HER3, such as those discussed above. In some embodiments, the anti-HER3 antibody is one or more of patritumab (U3-1287), duligotumab (MEHD-7945A), MM-111, LJM7116, RG-7116, tri-specific anti-EGFR/ERBB3 zybody, huHER3-8 and seribantumab (MM-121).

The anti-HER3 antibody can be administered at any suitable dose. For example, the antibody can be administered at about 9 mg/kg or more, about 12 mg/kg or more, about 15 mg/kg or more, or about 18 mg/kg or more. In some embodiments, the antibody can be administered at about 9 mg/kg or less, about 12 mg/kg or less, about 15 mg/kg or less, or about 18 mg/kg or less.

The anti-HER3 antibody can be administered by any suitable method. For example, in some embodiments the antibody is administered intravenously. However, the administration route is not limited to the intravenous one, but can be any other suitable one as well.

In some embodiments, the anti-HER3 antibody is administered one or more times every week or more frequently, or, every two weeks, or every three weeks, or less frequently.

In some embodiments, the treatment comprises administering an anti-HER3 antibody in combination with a tyrosine kinase inhibitor or HER inhibitor, such as an epidermal growth factor receptor inhibitor. The treatment can comprise administering an anti-HER3 antibody in combination with, for example, one or more of trastuzumab, T-DM1, lapatinib, pertuzumab, cetuximab, panitumumab gefitinib, afatinib, dacomitinib, KD-019 and erlotinib.

In some embodiments, the treatment comprises administering an anti-HER3 antibody in combination with a chemotherapy. The treatment can comprise administering an anti-HER3 antibody in combination with, for example, one or more of such as cisplatin, 5-fluoruracil, paclitaxel, capecitabine, and other chemotherapies.

In some embodiments, the treatment comprises administering an anti-HER3 antibody in combination with both a tyrosine kinase inhibitor or HER inhibitor and chemotherapy. The treatment can comprise administering an anti-HER3 antibody in combination with, for example, one or more of trastuzumab, T-DM1, lapatinib, pertuzumab, cetuximab, panitumumab, gefitinib, dacomitinib, KD-019, afatinib, dacomitinib, KD-019 and erlotinib, and one or more of cisplatin, carboplatin, gemcitabine, permetrexed, irinotecan, 5-fluoruracil, paclitaxel, docetaxel, capecitabine, and other chemotherapies.

In some embodiments, the treatment comprises administering an anti-HER3 antibody in combination with radiotherapy. In some embodiments, treatment comprises administering an anti-HER3 antibody in combination with radiotherapy and one or more of a tyrosine kinase inhibitor, HER inhibitor, and chemotherapy.

In some embodiments, anti-HER3 antibodies can be administered in combination with first-line treatments for metastatic or locally advanced head and neck cancer, such as radiotherapy or radiation therapy, cetuximab, cisplatin, and/or 5-fluoruracil.

In some embodiments, anti-HER3 antibodies can be administered in combination with first-line treatments for metastatic or locally advanced head and neck cancer, such as cetuximab, cisplatin, and/or 5-fluoruracil.

In some embodiments, anti-HER3 antibodies can be administered in combination with first-line treatments for NSCLC, such as erlotinib or platinum-based chemotherapy.

In some embodiments, anti-HER3 antibodies can be administered in combination with second-line treatments for NSCLC, such as docetaxel.

In some embodiments, anti-HER3 antibodies can be administered in combination with treatments for RAS wild-type cancer colorectal cancer and other cancer, such as cetuximab, panitumumab, and/or chemotherapy.

In some embodiments, anti-HER3 antibodies can be administered in combination with radiation, cisplatin, cetuximab, 5-fluoruracil, and/or other HER inhibitors or chemotherapies.

In some embodiments, anti-HER3 antibodies can be administered in combination with one or more of trastuzumab, paclitaxel, lapatinib, capecitabine, and/or other HER inhibitors or chemotherapies.

Test Kits

In some embodiments, the test kit contains materials for determining HRG content by IHC. Art IHC kit, for example, may contain a primary antibody against HRG, and a secondary antibody conjugated to a reporter enzyme, e.g., horseradish peroxidase. In some embodiments, the secondary antibody is replaced with a conjugated polymer that specifically recognizes the primary antibody.

EXAMPLES

The invention is further illustrated by the following examples. The examples are provided for illustrative purposes only, and are not to be construed as limiting the scope or content of the invention in any way.

Abbreviations: AE—adverse event; CI—confidence interval; CR—complete response; DLT—dose limiting toxicity; FAS—full analysis set; FFPE—formalin-fixed, paraffin-embedded; HR—hazard ratio; IN—intravenous; ITT—intent to treat; MTD—maximum tolerated dose; OS—overall survival; PD—progressive disease; ITS—progression-free survival; PH—proportional hazards; PO—oral; PR—partial response; SD—stable disease.

Example 1—Phase 1b/2 Clinical Trial

This and other examples provide the results of a randomized, placebo-controlled, double-blind Phase 1b/2 study designed to evaluate the safety and efficacy of patritumab in combination with erlotinib in EGFR-inhibitor treatment-naïve subjects with Stage IIIb/IV NSCLC who had progressed after at least 1 prior chemotherapy regimen.

The study comprised a Phase 1 b open-label, single-arm portion to assess safety and tolerability of patritumab in combination with erlotinib, and to determine the dosage for the Phase 2 portion, followed by a randomized, placebo-controlled Phase 2 portion to assess efficacy and safety of the combination therapy relative to erlotinib plus placebo, Based on Phase 1 study results in which a maximum tolerated dose was not reached, the preliminary human pharmacokinetic profile supported intravenous patritumab administration at or above 9 mg/kg once every 3 weeks to achieve circulating levels exceeding those showing maximal efficacy and pharmacodynamics in experimental animal models. A higher maintenance dose level of 18 mg/kg was also included to accommodate the possible effect of reduced tumor tissue penetration in the clinical setting relative to animal models. Due to the lack of dose limiting toxicity in a monotherapy Phase 1 study, the Phase 1b was designed as a dose-de-escalation study, with once daily oral administration of 150 mg of erlotinib and IV administration of 18 mg/kg patritumab every three weeks, with a provision for dose de-escalation from this maximal dose if it exceeded the MTD. As no DLTs were seen in this Phase 1b cohort, doses at this level and below were allowed in the Phase 2 portion.

In both portions of the study, subjects received 150 mg of erlotinib orally once daily. At the beginning of every 3 weeks treatment cycle, subjects received an IV infusion of patritumab or placebo (in Phase 2 portion). Three treatment regimens were evaluated: the combination of 150 mg erlotinib daily and 18 mg/kg patritumab every 3 weeks ("high dose"); the combination of 150 mg erlotinib daily and 18 mg/kg patritumab loading with 9 mg/kg patritumab maintenance every 3 weeks ("low dose"); and the combination of 150 mg erlotinib daily and placebo every 3 weeks ("placebo"). Tumors were to be assessed every 6 weeks (±3 days) up to the first 24 weeks of the study, then every 12 weeks (±7 days) independent of treatment cycle.

An "HRG high" subject was defined as a subject with observed soluble HRG concentration of higher than 980 pg/mL, the Quartile 3 of the sample set. Soluble HRC concentration was measured by the improved ELISA method disclosed herein.

In the study, 202 serum samples were collected from 215 randomized subjects. Concentration of soluble HRG in the samples were measured in duplicate in 5 batches, and mean values of the soluble HRG concentration were obtained for each subject. During the measurement, assay reproducibility was confirmed by repeat measurement of a control sample, which was recombinant heregulin in fetal bovine serum at a concentration of 4000 pg/mL. HRG data of greater than 0 pg/mL were obtained for 70 subjects. The Quartile 3 was determined using all the 202 samples.

The sample size for the Phase 2 portion was calculated based on a one-sided log-rank test with 80% power to detect a 50% improvement (that is, HR of 0.667) in median PFS of 3.3 vs 2.2 months between any patritumab arm compared to the control at a significance level of one-sided alpha=0.1.

The primary analyses for this study occurred when 162 PFS events (and 110 PFS events per comparison of patritumab 18 mg/kg+erlotinib and control arms, and of patritumab 9 mg/kg erlotinib and control arms) had been observed. At the point of primary analysis, the treatment assignment for all subjects was unblinded to designated study personnel for analysis after data were reconciled and cleaned, and a snapshot of the clean database was created. To minimize potential bias, individual treatment assignment was not divulged to subjects or Investigators until study closure.

All efficacy analyses were performed on the full analysis set, which includes all subjects in the randomized analysis set who received at least one dose of randomized study medication. The primary efficacy endpoint was PFS. PFS is defined as the time from the date of randomization to the earlier of the dates of the first objective documentation of radiographic disease progression or death due to any cause. A subject who was alive with no objective documentation of (radiographic) disease progression by the data cut-off date was to be censored at the date of the last evaluable tumor assessment. The key secondary efficacy endpoint, overall survival, was defined as the time from the date of randomization to death due to any cause and was analyzed in the same manner as the primary efficacy endpoint PFS.

The primary analysis for PFS used a stratified log-rank linear trend test for the dose-response relationship, followed by pair-wise comparisons of each patritumab arm and the control using the stratified log-rank test, accounting for the stratification factors at randomization: histology (Adenocarcinoma vs Non-Adenocarcinoma) and best response to prior therapy (CR/PR vs SD vs PD). Kaplan-Meier curves were generated for PFS and used to calculate medians and 95% CIs for each treatment group. Estimates of the HR between each patritumab arm and the control along with 95% CIs were calculated using a stratified Cox's proportional hazards model.

The primary analysis for PFS in HRG-high group on the FAS used a stratified log-rank test for the comparisons of each patritumab arm and the control and the comparison of the combined patritumab arm and the control. The stratification factors included histology (Adenocarcinoma vs Non-Adenocarcinoma) and best response to prior therapy (CR/PR/SD vs PD). Estimates of the FR between each patritumab arm and the control and between the combined patritumab arm and the control along with 95% CIs were calculated using a stratified. Cox's proportional hazards model with the same stratification factors used for the stratified log-rank test.

Unless otherwise indicated, tog-rank p-values and HRs for PFS and OS were based on the primary analysis adjusted for the stratification factors at randomization as described above.

The Phase 1b portion of the trial enrolled 7 subjects (4 male; median age [range], 68 years [48-78]) all of whom received the combination of 150 mg erlotinib daily and 18 mg/kg patritumab every 3 weeks. AEs grade≥3 occurred in 2 subjects: one grade 3 case each of pain, fatigue, headache, dehydration, diarrhea, and blood creatinine increase; none were related to patritumab. Three subjects had four serious AEs: grade 3 pain (unrelated to study treatment), grade 3 dehydration (erlotinib-related), and grade 1 decreased appetite (erlotinib- and patritumab-related) and grade 1 pyrexia (unrelated) in one subject. Most reported AEs were grade 1 or 2 and were considered erlotinib-related. The only patritumab-related AE reported in ≥2 subjects was decreased appetite (2 subjects).

No response was recorded and stable disease was noted in four subjects (83, 87, 90, and 117 days). All 7 subjects discontinued from study treatment due to disease progression; 6 subjects were followed until death, and 1 subject withdrew consent for follow-up.

No DLTs were reported during the phase 1b study. Therefore, the Phase 2 dose regimens were a patritumab 18 mg/kg loading dose, with subsequent administration of either a 9 mg/kg patritumab or 18 mg/kg patritumab maintenance dose every 3 weeks. Subjects were also administered 150 mg/day erlotinib during the phase 2 trial.

For the Phase 2 portion, 3 subjects were randomized but not treated, thus there were 212 subjects in the FAS and safety analysis set. The analysis results presented below are based on primary analyses of efficacy data (except for OS) from the locked database (as of data cut-off date Oct. 30, 2012), OS data was not mature yet at the time of primary analysis, and the preliminary results from updated OS analysis based on a data cut-off date of Apr. 19, 2013 are presented below.

Dispositions of the 215 subjects enrolled into the randomized. Phase 2 portion of the study are summarized in Table 1. Demographic information for the full analysis set is summarized in Table 2. There was no meaningful difference among treatment groups with respect to demographic characteristics.

TABLE 1

| | | | | | |
|---|---|---|---|---|---|
| | Phase 2 Subject Disposition | | | | |
| | Subject Accounting | Placebo + erlotinib (N = 71) | 18 mg/kg + erlotinib (N = 72) | 9 mg/kg + erlotinib (N = 72) | Total Phase 2 (N = 215) |
| Treatment Status | Enrolled/Randomized but Not Dosed | 0 | 2 (2.8%) | 1 (1.4%) | 3 (1.4%) |
| | Ongoing on the Study Treatment | 5 (7.0%) | 5 (6.9%) | 6 (8.3%) | 16 (7.4%) |
| | Discontinued from Study Treatment | 66 (93.0%) | 65 (90.3%) | 65 (90.3%) | 196 (91.2%) |
| Primary Reason for Discontinuing Study Treatment | Adverse Event | 5 (7.0%) | 7 (9.7%) | 6 (8.3%) | 18 (8.4%) |
| | Lost to Follow-up | 0 | 0 | 0 | 0 |
| | Death | 4 (5.6%) | 11 (15.3%) | 2 (2.8%) | 17 (7.9%) |
| | Protocol Violation | 0 | 0 | 0 | 0 |
| | Subject Withdrew Consent | 3 (4.2%) | 2 (2.8%) | 4 (5.6%) | 9 (4.2%) |
| | Study Terminated by Sponsor | 0 | 0 | 0 | 0 |
| | Progressive Disease (Radiographic Progression) | 50 (70.4%) | 42 (58.3%) | 45 (62.5%) | 137 (63.7%) |
| | Other | 4 (5.6%) | 3 (4.2%) | 8 (11.1%) | 15 (7.0%) |
| On-Study Death[a] | | 13 (18.3%) | 20 (27.8%) | 9 (12.5%) | 42 (19.5%) |
| Primary Cause of On-Study Death | Adverse Event | 5 (7.0%) | 11 (15.3%) | 4 (5.6%) | 20 (9.3%) |
| | Disease Progression | 8 (11.3%) | 8 (11.1%) | 4 (5.6%) | 20 (9.3%) |
| | Unknown | 0 | 0 | 1 (1.4%) | 1 (0.5%) |
| | Other | 0 | 1 (1.4%) | 0 | 1 (0.5%) |

Notes:

Percentages are based on the number of subjects in the Enrolled/Randomized Analysis Set.

[a]On-Study Death = Y if the date of death occurred on or after the date of first drug administration and within the AE collection period (up to 53 days after the last dose of patritumab or more than 30 days after the last dose of erlotinib, whichever is later).

TABLE 2

| | | | | |
|---|---|---|---|---|
| | Demographic and Baseline Characteristics (Full Analysis Set) | | | |
| | Placebo + erlotinib (N = 71) | 18 mg/kg + erlotinib (N = 70) | 9 mg/kg + erlotinib (N = 71) | Total (N = 212) |
| Age (yrs) [a] | | | | |
| Median | 60.0 | 62.0 | 65.0 | 62.5 |
| Minimum | 35 | 41 | 44 | 35 |
| Maximum | 88 | 82 | 84 | 38 |
| <60 | 33 (46.5%) | 28 (40.0%) | 24 (33.8%) | 85 (40.1%) |
| >=60 | 38 (53.5%) | 42 (60.0%) | 47 (66.2%) | 127 (59.9%) |
| Gender | | | | |
| Male | 43 (60.6%) | 38 (54.3%) | 48 (67.6%) | 129 (60.8%) |
| Female | 38 (39.4%) | 32 (45.7%) | 23 (32.4%) | 83 (39.2%) |
| Race | | | | |
| White | 69 (97.2%) | 68 (97.1%) | 71 (100.0%) | 208 (98.1%) |
| Black or African American | 1 (1.4%) | 1 (1.4%) | 0 | 2 (0.9%) |
| Asian | 0 | 1 (1.4%) | 0 | 1 (0.5%) |
| Other/Specify | 1 (1.4%) | 0 | 0 | 1 (0.5%) |

TABLE 2-continued

| Demographic and Baseline Characteristics (Full Analysis Set) | | | |
|---|---|---|---|
| | Placebo + erlotinib (N = 71) | 18 mg/kg + erlotinib (N = 70) | 9 mg/kg + erlotinib (N = 71) | Total (N = 212) |
| Weight (kg) | | | |
| n | 71 | 70 | 71 | 212 |
| Mean | 74.68 | 73.59 | 72.34 | 73.53 |
| SD | 14.337 | 17.506 | 14.369 | 15.422 |
| Median | 74.00 | 72.00 | 72.30 | 72.55 |
| Minimum | 42.6 | 44.0 | 42.0 | 42.0 |
| Maximum | 108.6 | 121.0 | 114.0 | 121.0 |
| Smoking Status | | | |
| Never | 5 (7.0%) | 10 (14.3%) | 11 (15.5%) | 26 (12.3%) |
| Current | 13 (18.3%) | 12 (17.1%) | 9 (12.7%) | 34 (16.0%) |
| Former | 53 (74.6%) | 48 (68.6%) | 51 (71.8%) | 152 (71.7%) |
| Pack Years (PY) | | | |
| <=15 PY | 11 (15.5%) | 9 (12.9%) | 7 (9.9%) | 27 (12.7%) |
| >15 PY | 50 (70.4%) | 43 (61.4%) | 47 (66.2%) | 140 (66.0%) |
| Missing | 10 (14.1%) | 18 (25.7%) | 17 (23.9%) | 45 (21.2%) |

Notes:
Denominator for percentages is the number of subjects in the FAS.
[a]: Age in years is calculated using the informed consent date and the birth date Subject baseline characteristics with regard to NSCLC history and prior therapy are shown in Table 3. Subjects generally appeared to be well balanced among treatment groups.

TABLE 3

| Baseline Prognostic and Disease Characteristics (Full Analysis Set) | | | |
|---|---|---|---|
| | Placebo + erlotinib (N = 71) | 18 mg/kg + erlotinib (N = 70) | 9 mg/kg + erlotinib (N = 71) | Total (N = 212) |
| Baseline ECOG Performance Status | | | |
| 0 Fully Active | 25 (35.2%) | 33 (47.1%) | 30 (42.3%) | 88 (41.5%) |
| 1 Restricted in Physically Strenuous Activity | 46 (64.8%) | 37 (52.9%) | 41 (57.7%) | 124 (58.5%) |
| Histology | | | |
| Adenocarcinoma | 42 (59.2%) | 46 (65.7%) | 44 (62.0%) | 132 (62.3%) |
| Squamous | 21 (29.6%) | 19 (27.1%) | 23 (32.4%) | 63 (29.7%) |
| Other | 8 (11.3%) | 5 (7.1%) | 4 (5.6%) | 17 (8.0%) |
| NSCLC Tumor Staging at Study Entry (CRF) | | | |
| IIIB | 7 (9.9%) | 5 (7.1%) | 9 (12.7%) | 21 (9.9%) |
| IV | 64 (90.1%) | 65 (92.9%) | 62 (87.3%) | 191 (90.1%) |
| Time from Initial Diagnosis of NSCLC to Study Treatment (months) | | | |
| <6 months | 10 (14.1%) | 16 (22.9%) | 14 (19.7%) | 40 (18.9%) |
| 6-12 months | 37 (52.1%) | 33 (47.1%) | 35 (49.3%) | 105 (49.5%) |
| >12 months | 24 (33.8%) | 21 (30.0%) | 22 (31.0%) | 67 (31.6%) |
| Number of Prior NSCLC Therapies | | | |
| 0 | 0 | 0 | 0 | 0 |
| 1 | 47 (66.2%) | 50 (71.4%) | 48 (67.6%) | 145 (68.4%) |
| 2 | 24 (33.8%) | 19 (27.1%) | 22 (31.0%) | 65 (30.7%) |
| 3 | 0 | 1 (1.4%) | 1 (1.4%) | 2 (0.9%) |
| Best Response to Prior Chemotherapy[a] | | | |
| CR/PR | 23 (32.4%) | 19 (27.1%) | 17 (23.9%) | 59 (27.8%) |
| SD | 29 (40.8%) | 28 (40.0%) | 34 (47.9%) | 91 (42.9%) |
| PD | 19 (26.8%) | 23 (32.9%) | 20 (28.2%) | 62 (29.2%) |

TABLE 3-continued

| Baseline Prognostic and Disease Characteristics (Full Analysis Set) | | | |
|---|---|---|---|
| | Placebo + erlotinib (N = 71) | 18 mg/kg + erlotinib (N = 70) | 9 mg/kg + erlotinib (N = 71) | Total (N = 212) |
| Exposure to Prior Platinum Therapy | | | | |
| Yes | 70 (98.6%) | 70 (100.0%) | 70 (98.6%) | 210 (99.1%) |
| No | 1 (1.4%) | 0 | 1 (1.4%) | 2 (0.9%) |
| Prior Radiation Therapy | | | | |
| Yes | 24 (33.8%) | 25 (35.7%) | 22 (31.0%) | 71 (33.5%) |
| No | 47 (66.2%) | 45 (64.3%) | 49 (69.0%) | 141 (66.5%) |

Notes:

Percentages reflect proportion of subjects in Full Analysis Set (FAS). Baseline = last non-missing value before initial administration of study treatment.

[a]If a subject has two lines of prior chemotherapy regimens, the best response to the most recent chemotherapy regimen (excluding 'Not Applicable') was used.

Figure 1:
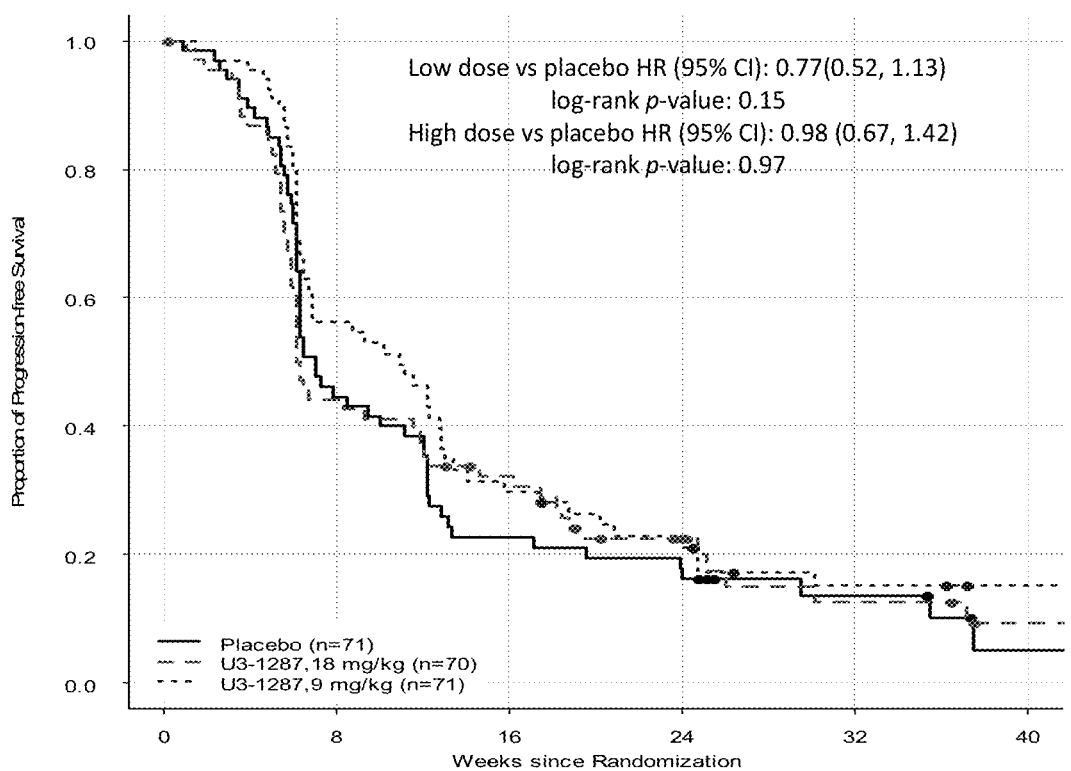
FIG. 1 depicts progression-free survival (showing high- and low-dose patritumab+erlotinib vs. placebo+erlitonib) for all subjects from the study in Example 2.
Figure 2:
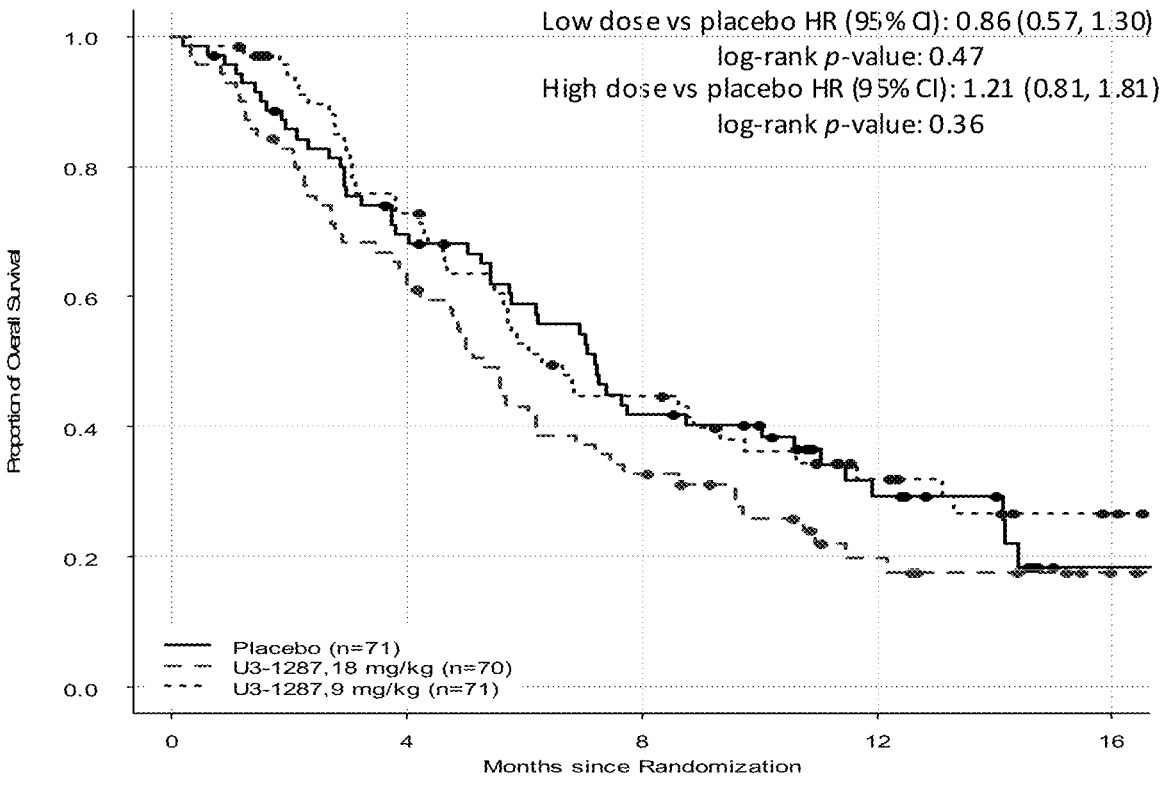
FIG. 2 depicts overall survival (showing high- and low-dose patritumab+erlotinib vs. placebo+erlitonib) for all subjects from the study in Example 2.

Example 2—Progression Free Survival and Overall Survival in Full Analysis Set Primary analysis of PFS for the FAS is presented in Table 4. Kaplan-Meier estimates of progression-free survival in the FAS are presented in FIG. 1 (showing high- and low-dose patritumab+erlotinib vs. placebo+erlitonib). Overall Survival (OS) results in the unselected FAS are presented in Table 5 and in FIG. 2 (showing high- and low-dose patritumab+erlotinib vs. placebo+erlitonib). There was no significant improvement in PFS or OS for the combination of patritumab with erlotinib as compared to erlotinib plus placebo in the full analysis set, and the study was considered as negative for the unselected ITT population.

The number of subjects with the response being CR/PR in low- and high-dose patritumab treatment groups were respectively 9 (12.9%) and 5 (7.1%) vs placebo 4 (5.6%).

TABLE 4

| Analysis of Progression-Free Survival in Full Analysis Set | | | |
|---|---|---|---|
| | Placebo + erlotinib (N = 71) | 18 mg/kg + erlotinib (N = 70) | 9 mg/kg + erlotinib (N = 71) |
| Subjects (%) with events | 59 (83.1%) | 58 (82.9%) | 52 (73.2%) |
| Subjects (%) without events (censored) | 12 (16.9%) | 12 (17.1%) | 19 (26.8%) |

TABLE 4-continued

| Analysis of Progression-Free Survival in Full Analysis Set | | | |
|---|---|---|---|
| | Placebo + erlotinib (N = 71) | 18 mg/kg + erlotinib (N = 70) | 9 mg/kg + erlotinib (N = 71) |
| Time to event (months) [a] | | | |
| Median | 1.6 | 1.4 | 2.5 |
| 95% CI for Median | [1.4; 2.6] | [1.3; 2.7] | [1.5; 3.0] |
| Stratified Logrank P-Value [b] | | 0.9735 | 0.1512 |
| Hazard Ratio (relative to Placebo) [b] | | 0.978 | 0.770 |
| 95% CI | | [0.674; 1.420] | [0.523; 1.131] |
| 80% CI | | [0.767; 1,248] | [0.598; 0.990] |
| P-value for Hazard Ratio | | 0.9075 | 0.1828 |

Notes:

PFS is defined as the time from the randomization date to the date of the first objective documentation of disease progression or death resulting from any cause, whichever comes first.

[a] Kaplan-Meier Estimate. CI for median was computed using the Brookmeyer-Crowley method.

[b] Stratified log-rank and stratified Cox PH were stratified by best response to prior therapy and histology subtype (Adenocarcinoma vs. Non-Adenocarcinoma).

TABLE 5

| Analysis of Overall Survival in Full Analysis Set | | | |
|---|---|---|---|
| | Placebo + erlotinib (N = 71) | 18 mg/kg + erlotinib (N = 70) | 9 mg/kg + erlotinib (N = 71) |
| Subjects (%) with events | 48 (67.6%) | 54 (77.1%) | 46 (64.8%) |
| Subjects (%) without events (censored) | 23 (32.4%) | 16 (22.9%) | 25 (35.2%) |
| Time to event (months) [a] | | | |
| Median | 7.2 | 5.3 | 6.3 |
| 95% CI for Median | [5.4; 10.6] | [4.0; 6.9] | [5.4; 9.3] |
| Stratified Logrank P-Value [b] | | 0.3823 | 0.3673 |
| Hazard Ratio (relative to Placebo) [b] | | 1.208 | 0.858 |
| 95% CI | | [0.807; 1.808] | [0.566; 1.301] |
| 80% CI | | [0.928; 1.572] | [0.653; 1.127] |
| P-value for Hazard Ratio | | 0.3585 | 0.4712 |

Notes:

OS is defined as the time from the randomization date to the date of death.

[a] Kaplan-Meier Estimate. CI for median was computed using the Brookmeyer-Crowley method.

[b] Stratified log-rank and stratified Cox PH were stratified by best response to prior therapy and histology subtype (adenocarcinoma vs. non-adenocarcinoma).

Figure 3:
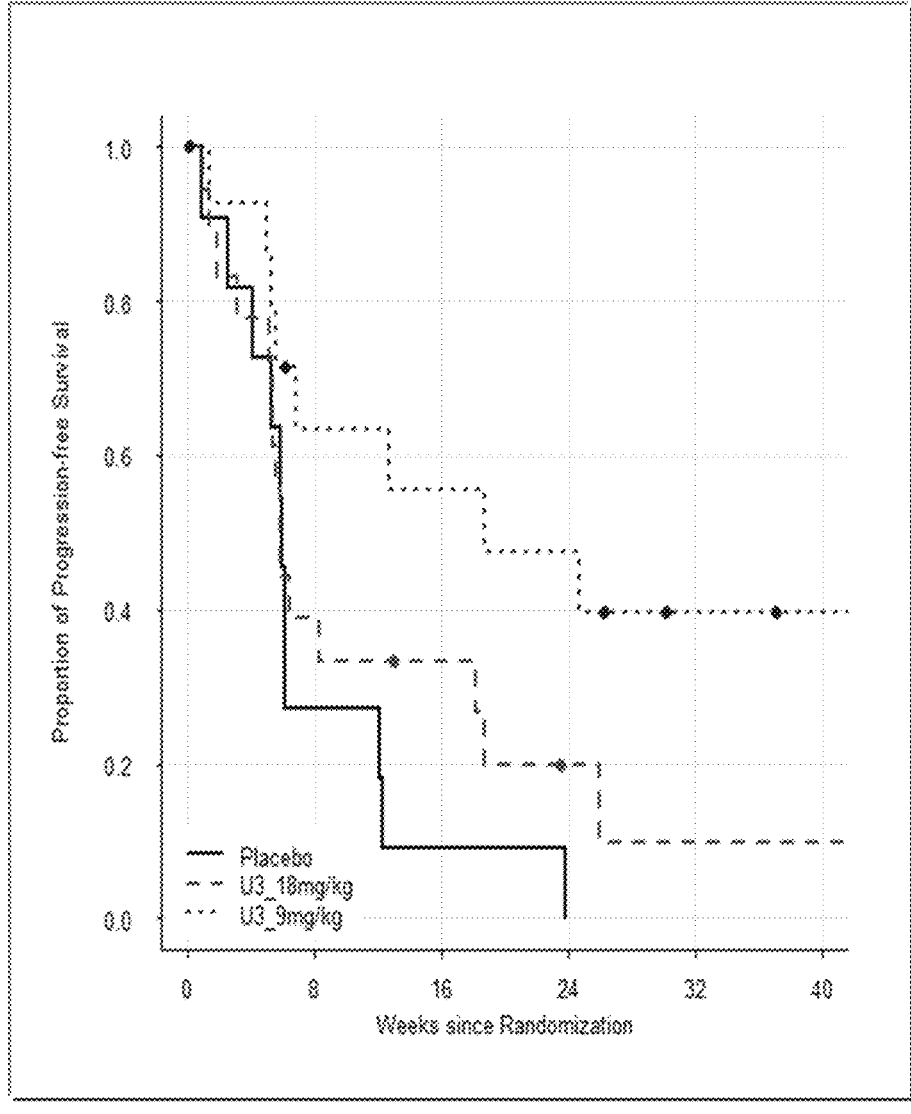
FIG. 3 depicts progression free survival (showing high- and low-dose patritumab+erlotinib vs. placebo+erlitonib)

Example 3—Progression Free Survival in Subjects
with Tumors Expressing High Soluble HRG Levels Kaplan-Meier estimates of progression-free survival in subjects with tumors expressing high HRG at a protein level, defined as protein concentration>980 pg/mL, are presented in FIG. 3 (showing high- and low-dose patritumab+erlotinib vs. placebo+erlitonib) and FIG. 4 (showing pooled patritumab erlotinib vs. placebo+erlitonib).

Example 4—Overall Survival in Subjects with
Tumors Expressing High Soluble HRG Levels Preliminary OS results in the subset of subjects with tumors expressing high levels of HRG at a protein level, defined as protein concentration>980 pg/mL, are presented in FIG. 5 (showing high- and low-dose patritumab+erlotinib vs. placebo+erlitonib) and FIG. 6 (showing pooled patritumab+erlotinib vs. placebo+erlitonib).

Example 5—Efficacy in Subjects with Tumors
Expressing Low Soluble HRG Levels

In contrast with subjects whose tumors expressed high levels of HRG, subjects with tumors expressing low levels of HRG showed no clear treatment difference in PFS and OS. Kaplan-Meier estimates of PFS in subjects with tumors expressing low HRG at a protein level, defined as protein concentration<980 pg/mL, are presented in FIG. 7 (showing pooled patritumab+erlotinib vs. placebo+erlitonib). Kaplan-Meier estimates of OS in subjects with tumors expressing low HRG at a protein level, defined as protein concentration<980 pg/mL, are presented in FIG. 8 (showing pooled patritumab+erlotinib vs. placebo+erlitonib).

Example 6—Potential Cut-off Values for Soluble
HRG Protein Concentration vs. Clinical Benefit Data was used to calculate hazard ratios between the pooled dose of patritumab and placebo based on several potential cut-off values for HRG protein concentration. These hazard ratios are shown in Table 6. It appears that higher HRG expression is generally correlated with a greater clinical benefit in terms of PFS. Raising the cutoff from 980 pg/mL to, for example, 3000 pg/mL results in additional improvement in the average benefit as judged by the hazard ratio.

TABLE 6

| Hazard ratios and p-values for PFS in the soluble HRG high group as a function of cutoff | | | |
| --- | --- | --- | --- |
| HRG protein concentration cut-off (pg/mL) | n | HR for PFS (pooled dose vs placebo) | Log-rank p-value for PFS |
| 0 (median) | 66 | 0.58 | 0.08 |
| 980 (Q3) | 46 | 0.41 | 0.02 |
| 1622.5 | 39 | 0.31 | 0.01 |
| 2000 | 34 | 0.28 | 0.008 |
| 3000 | 30 | 0.24 | 0.006 |
| 4000 | 27 | 0.26 | 0.01 |
| 5000 | 23 | 0.40 | 0.13 |

Example 7—Improved ELISA Method

ELISAs were performed to detect soluble HRG in serum samples using the human NRG1-b1/HRG1-b1 DuoSet ELISA Development kit (R&D Systems, Inc., Minneapolis, MN; catalog #DY377). To perform the assays, 100 µl of capture antibody solution containing 4.0 µg/ml mouse anti-human NRG1-b1 in PBS was added to each well of a 96-well plate. The capture antibody solution was prepared by diluting 180-fold with PBS (e.g., 5 µl of the original solution in the kit was added to 895 µl of PBS for 8 wells). The plates were then covered and kept at room temperature overnight.

The capture antibody solution was then aspirated and the wells were washed by either (i) a "control wash" method in which each well was filled with 400 µl wash buffer using a squirt bottle after which the wash buffer was removed, and the process was repeated two additional times for a total of three washes, or (ii) an "improved wash" method. For the "improved wash" method, 180 µl of wash buffer was added to each well using a multichannel pipettor and the wash buffer was cycled by performing a piston action 20 times until the wash buffer was bubbly. The wash buffer was then aspirated and the cycling was repeated with another 180 µl of wash buffer using a piston action 20 times until the wash buffer was bubbly. The wash buffers was then aspirated and a rinse step was performed in which 200 µl of wash buffer was added to each well and then immediately aspirated, ensuring that all bubbles were removed. Thus, the improved wash method involved two wash steps using a piston action and one rinse step. The wash buffer contained 0.05% TWEEN® 20 detergent in PBS, pH 7.2-7.4 and was prepared by diluting the provided solution 25-fold with distilled water (i.e., 4 ml of original solution+96 ml of distilled water).

300 µl of a reagent diluent containing 1% BSA in PBS, pH 7.2-7.4, 0.2 um filtered was then added to each well and the plate was covered and kept at room temperature for one hour. During this time, a heregulin standard was prepared (described below). Following the 1 hour incubation, the reagent diluent was aspirated and the wells were washed using either the control wash method or the improved wash method described above.

100 µl of undiluted serum or plasma (or heregulin standard) was then added to each well, after which the plate was covered and kept at room temperature for two hours. The sample (or standard) was aspirated and the wells were washed using either the control wash method or the improved wash method.

100 µl of a detection antibody solution containing 150 ng/ml biotinylated goat anti-human NRG1-b1 antibody in reagent diluent was then added to each well and the plates were covered and kept at room temperature for two hours. The detection antibody solution was prepared by diluting the original solution 180-fold with reagent diluent (e.g. 5 µl of original solution+895 µl of Reagent Diluent for 8 wells). Although the kit instructions call for the addition of 2% heat inactivated normal goat serum (NGS), NGS was not included in the detection antibody solution for these experiments.

The detection antibody solution was aspirated and the wells were washed using either the control wash method or the improved wash method. 100 µl of a working solution of streptavidin-HRP solution was then added to each well and allowed to incubate at room temperature for 20 minutes under shaded conditions. The vial of streptavidin-HRP solution provided with the kit contained 1.0 mL of streptavidin conjugated to HRP and the working concentration was prepared by diluting the contents of the vial with reagent diluent as directed on the vial label. Following the 20 minute incubation, the streptavidin-HRP solution was aspirated and the wells were washed using either the control wash method or the improved wash method.

100 µl of substrate solution containing a 1:1 mixture of $H_2O_2$ (Color reagent A) and tetramethylbenzidine (Color reagent B) was then added to each well and allowed to incubate at room temperature for 20 minutes under shaded conditions after which 50 µl of stop solution was added to each well. The stop solution contained $2\text{-}NH_2SO_4$. The optical density of each well was then measured at $OD_{450}$ (correction by $OD_{570}$).

Preparation of the heregulin Standard was as follows:

TABLE 7

| Preparation of heregulin Standard | | |
|---|---|---|
| | Final concentration | |
| Stock Solution | 275 ng/ml | Compound + Reagent Diluent 0.5 ml |
| A | 4000 pg/ml | Stock 5 µl + Reagent Diluent 337 ml |
| B | 2000 pg/ml | A 200 µl + Reagent Diluent 200 µl |
| C | 1000 pg/ml | B 200 µl + Reagent Diluent 200 µl |
| D | 500 pg/ml | C 200 µl + Reagent Diluent 200 µl |
| E | 250 pg/ml | D 200 µl + Reagent Diluent 200 µl |
| F | 125 pg/ml | E 200 µl + Reagent Diluent 200 µl |
| G | 62.5 pg/ml | F 200 µl + Reagent Diluent 200 µl |
| H | 0 pg/ml | Reagent Diluent 200 µl |

The attempts to detect soluble HRG using the published kit instructions with the control wash method) failed consistently. However, a varied range of soluble HRG in serum was be able to be measured with high reproducibility using the process with the improved wash method.

Example 8—Biomarker Identification

The HRG biomarker was identified by analysing the anti-tumor activity of the anti-HER3 antibody U3-1287 on various human cancer xenografts in vivo and analysis of the expression of HRG of these cell lines in vitro. Human tumor cell lines of various indications were grown as xenografts in mice and treated with the anti-HER3 antibody U3-1287 for several weeks. Inhibition of tumor growth was analysed by comparing the tumor volumes of control mice and mice treated with U3-1287. Human tumor cell lines were grown in vitro and analysed for HRG protein expression by Western blotting. The results of this analysis are shown in Table 8. Basal activity of HER3 as measured by Western blotting did not correlate with in vivo efficacy of U3-1287, predominantly in FISH positive breast cancer models. In contrast, expression of HRG correlated very well with in vivo efficacy of U3-1287, as seen for 15 of the 17 models analyzed.

TABLE 8

Retrospective in vitro analysis of cell lines used for in vivo xenografts

| Cell Line | Indication | HER (WB) | Phospho HER3 (WB) | HRG (WB) | In vivo efficacy (SA) | Correlation |
|---|---|---|---|---|---|---|
| Sum225 | BC FISH + ve | + | + | − | No | Yes |
| MDA-MB453 | BC FISH + ve | + | + | − | No | Yes |
| BT474 | BC FISH + ve | + | + | − | No | Yes |
| HCC 1569 | BC FISH + ve | + | + | − | No | Yes |
| ZR75-1 | BC FISH + ve | + | − | − | No | Yes |
| MCF-7 | BC FISH + ve | + | − | − | No | Yes |
| T47D | BC FISH + ve | + | + | − | No | Yes |
| NCI-H441 | NSCLC | + | + | − | No | Yes |
| A549 | NSCLC | + | + | + | Yes | Yes |
| Calu-3 | NSCLC | + | + | + | Yes | Yes |
| NC-H1975 | NSCLC | + | + | + | Yes | Yes |
| A375 | Melanoma | + | − | − | No | Yes |
| HT-144 | Melanoma | + | − | − | No | Yes |
| HT-29 | Colon | + | + | − | Yes | No |
| MKN-45 | Gastric | + | + | − | Yes | No |
| BxPC3 | Pancreas | + | + | + | Yes | Yes |
| FaDu | Head&Neck | + | + | + | Yes | Yes |

U3-1287 efficacy was determined in vitro by measuring reduction of phospho-HER3 and phospho-AKT levels. Basal HER3 phosphorylation could be blocked in cell tines that endogenously express heregulin (A549) as well as in cells that do not have basal HER3 activation but were stimulated with exogenous heregulin (CaOV3). U3-1287 efficacy results are shown in FIG. 9.

Unexpectedly cells that have basal HER3 phosphorylation but do not express heregulin showed no efficacy upon U3-1287 treatment (BT474 basal) and even more surprisingly, this could be overcome by exogenously added heregulin (BT474+HRG), as shown in FIG. 10.

INCORPORATION BY REFERENCE

The entire disclosure of each of the patent documents and scientific articles cited herein is incorporated by reference for all purposes.

What is claimed is:

1. A method of treating a human subject with a locally advanced or metastatic non-small cell lung cancer (NSCLC) that is characterized as having a high heregulin (HRG) expression at a protein level, comprising:
   (a) obtaining a tumor sample from a human subject with a locally advanced or metastatic NSCLC;
   (b) determining the HRG expression at the protein level in the tumor sample;
   (c) selecting the subject for treatment when the tumor sample has a high HRG expression at the protein level; and
   (c) administering an anti-HER3 antibody to the subject;
   wherein HRG is the only gene for which gene expression at the protein level is assessed for the purposes of selecting treatment for the subject.

2. The method of claim 1, wherein determining the HRG expression at the protein level comprises using ELISA or immunohistochemistry techniques and the high HRG expression at the protein level is higher than 980 pg/mL in a tumor sample from the subject.

3. The method of claim 1, wherein the subject expresses a wild-type epidermal growth factor receptor (EGFR) or does not express a mutant EGFR.

4. The method of claim 1, wherein the anti-HER3 antibody is selected from the group consisting of patritumab, duligotumab (MEHD-7945A), seribantumab (MM-121), MM-111, LJM716, RG-7116, tri-specific anti-EGFR/ ERBB3 zybody, and huHER3-8.

5. The method of claim 1 further comprising administering one or more of (i) a HER inhibitor, (ii) a chemotherapy, (iii) radiation, and (iv) another targeted agent.

6. The method of claim 5, wherein the HER inhibitor is selected from the group consisting of trastuzumab, T-DM1, lapatinib, pertuzumab, cetuximab, panitumumab gefitinib, afatinib, dacomitinib, KD-019 and erlotinib.

7. The method of claim 5, wherein the chemotherapy is selected from the group consisting of cisplatin, carboplatin, gemcitabine, pemetrexed, irinotecan, 5-fluoruracil, paclitaxel, docetaxel, and capecitabine.

8. The method of claim 1, further comprising administering (i) cetuximab and (ii) cisplatin or carboplatin.

* * * * *